US012558239B2

(12) United States Patent
Larose et al.

(10) Patent No.: US 12,558,239 B2
(45) Date of Patent: Feb. 24, 2026

(54) EXOSKELETON, ORTHOSIS, WEARABLE DEVICE OR MOBILE ROBOTS USING MAGNETORHEOLOGICAL FLUID CLUTCH APPARATUS

(71) Applicant: EXONETIK INC., Sherbrooke (CA)

(72) Inventors: Pascal Larose, Sherbrooke (CA); Marc Denninger, Sherbrooke (CA); Jean-Sebastien Plante, Sherbrooke (CA); Jean-Philippe Lucking Bigue, Sherbrooke (CA); Catherine Veronneau, Waterville (CA)

(73) Assignee: EXONETIK INC., Sherbrooke (CA)

( * ) Notice: Subject to any disclaimer, the term of this patent is extended or adjusted under 35 U.S.C. 154(b) by 70 days.

(21) Appl. No.: 18/436,390

(22) Filed: Feb. 8, 2024

(65) Prior Publication Data

US 2024/0173149 A1 May 30, 2024

Related U.S. Application Data

(63) Continuation of application No. 16/610,337, filed as application No. PCT/CA2018/050570 on May 14, 2018.

(Continued)

(51) Int. Cl.
A61H 3/00 (2006.01)
A61F 2/70 (2006.01)
(Continued)

(52) U.S. Cl.
CPC .............. *A61F 2/70* (2013.01); *A61F 5/0127* (2013.01); *A61F 5/013* (2013.01); *A61H 1/0281* (2013.01);
(Continued)

(58) Field of Classification Search
CPC .. A61H 1/0281; A61H 3/00; A61H 2003/001; F16D 37/02; A61F 2/70; A61F 5/0127; A61F 5/013
See application file for complete search history.

(56) References Cited

U.S. PATENT DOCUMENTS

| | | | |
|---|---|---|---|
| 5,092,322 A | 3/1992 | Gantz | |
| 2006/0249315 A1 | 11/2006 | Herr et al. | |

(Continued)

FOREIGN PATENT DOCUMENTS

| | | |
|---|---|---|
| CN | 101637913 A | 2/2010 |
| JP | 2015222542 A | 12/2015 |

(Continued)

*Primary Examiner* — Timothy A Stanis
(74) *Attorney, Agent, or Firm* — NORTON ROSE FULBRIGHT CANADA LLP

(57) ABSTRACT

A system comprises one or more wearable devices including a first body interface adapted to be secured to a first bodily part. A second body interface is adapted to be secured to a second bodily part separated from the first bodily part by a physiological joint. One or more joints provide one or more degrees of freedom between the first body interface and the second body interface. A magnetorheological (MR) fluid actuator unit comprises one or more power sources. An MR fluid clutch apparatus receiving torque from the at least one power source, the at least one MR fluid clutch apparatus operable to generate a variable amount of torque transmission when subjected to a magnetic field. A transmission couples the MR fluid actuator unit to the wearable device for converting torque from the MR fluid actuator unit to relative movement of the body interfaces with respect to one another.

19 Claims, 24 Drawing Sheets

Related U.S. Application Data

(60) Provisional application No. 62/505,392, filed on May 12, 2017.

(51) Int. Cl.

| | |
|---|---|
| *A61F 5/01* | (2006.01) |
| *A61H 1/02* | (2006.01) |
| *B25J 9/00* | (2006.01) |
| *F16D 37/02* | (2006.01) |
| *A61F 2/68* | (2006.01) |
| *A61F 2/74* | (2006.01) |
| *F16D 37/00* | (2006.01) |

(52) U.S. Cl.
CPC ............ *B25J 9/0006* (2013.01); *F16D 37/02* (2013.01); *A61F 2002/6845* (2013.01); *A61F 2002/6863* (2013.01); *A61F 2/74* (2021.08); *A61F 2/741* (2021.08); *A61F 2005/0155* (2013.01); *A61H 2201/1207* (2013.01); *A61H 2201/1616* (2013.01); *A61H 2201/165* (2013.01); *F16D 2037/004* (2013.01)

(56) References Cited

U.S. PATENT DOCUMENTS

| | | | |
|---|---|---|---|
| 2007/0162152 | A1 | 7/2007 | Herr et al. |
| 2008/0097269 | A1 | 4/2008 | Weinberg et al. |
| 2010/0160844 | A1 | 6/2010 | Gilbert et al. |
| 2011/0164949 | A1 | 7/2011 | Kim et al. |
| 2012/0090938 | A1 | 4/2012 | Maas et al. |
| 2012/0184880 | A1 | 7/2012 | Doyle |
| 2012/0330198 | A1* | 12/2012 | Patoglu ................ A61H 1/0281 |
| | | | 601/33 |
| 2013/0175132 | A1 | 7/2013 | Battlogg |
| 2013/0289452 | A1* | 10/2013 | Smith ................ A63B 21/4009 |
| | | | 601/33 |
| 2013/0304084 | A1 | 11/2013 | Beira et al. |
| 2014/0158839 | A1 | 6/2014 | Doyle |
| 2015/0001269 | A1 | 1/2015 | Sacksteder |
| 2015/0107395 | A1 | 4/2015 | Kermani et al. |
| 2016/0038368 | A1* | 2/2016 | Lee ..................... A61H 1/0244 |
| | | | 623/24 |
| 2018/0072189 | A1 | 3/2018 | Plante et al. |
| 2018/0304457 | A1 | 10/2018 | Hutson et al. |

FOREIGN PATENT DOCUMENTS

| | | | | |
|---|---|---|---|---|
| WO | 2009117827 | A1 | 10/2009 | |
| WO | 2013186705 | A2 | 12/2013 | |
| WO | 2016134472 | A1 | 9/2016 | |
| WO | WO-2017031585 | A1 * | 3/2017 | .......... A63B 21/153 |
| WO | 2017064315 | A1 | 4/2017 | |
| WO | 2017083970 | A1 | 5/2017 | |

* cited by examiner

Processor unit

Processor unit

Processor unit

Processor
unit

EXOSKELETON, ORTHOSIS, WEARABLE DEVICE OR MOBILE ROBOTS USING MAGNETORHEOLOGICAL FLUID CLUTCH APPARATUS

CROSS-REFERENCE TO RELATED APPLICATION

The present application is a continuation of U.S. patent application Ser. No. 16/610,337, filed on Nov. 1, 2019, which is a 371 application of PCT Application No. PCT/CA2018/050570, filed on May 14, 2018 and which claims the priority of U.S. Provisional Patent Application No. 62/505,392, filed on May 12, 2017, the contents of which are incorporated herein by reference.

TECHNICAL FIELD

The present application relates generally to the field of exoskeletons or orthoses/orthotics, and more particularly, to exoskeletons or orthosis systems using magnetorheological (MR) fluid clutch apparatuses.

BACKGROUND OF THE ART

The use of exoskeletons, orthoses or prostheses on humans may be desirable to enhance human capacities or restore human capabilities. In some cases, the objective is the reduction of the amount of human effort required to perform a task or function and in other cases the objective may be to amplify human capacity. In some cases, the objective is to restore human function. In some other cases, the exoskeleton could have the function of generating energy for a later use. In many cases, there is an exchange or energy between the human body and the exoskeleton and this exchange of energy occurs through mechanical contact between the user's limbs and the exoskeleton interface.

Many exoskeletons have been introduced over the years. In some cases, the exoskeleton assists the human by consuming energy coming from fuel or batteries, for example. Typically, exoskeletons use electric motors to actuate the joints, although hydraulic or pneumatic actuation may also be found. Such actuator types may have a relatively low mechanical bandwidth, and may cause discomfort to the user. This discomfort often disrupts device function, limits other human functions (e.g.: running) and decreases the interest in humans wearing such devices.

Since the interaction between the human body and the exoskeleton implies mechanical force distribution on soft tissues surrounding the joint and limb segment, exoskeletons may need soft or resilient contact patches to transfer a load to human, which may result in an ineffective power transfer.

Exoskeletons generally employ a motor/generator unit that operates in concert with human power to provide power to the joint actuators. Internal combustion engines, turbines, batteries, air pressure turbines or any other power source may be used to generate the energy required by the actuator. Some exoskeletons use mechanical (e.g.: gears, linkages), hydraulic or pneumatic transmissions to route the power where the human effort needs to be augmented or replaced. This type of wearable or equipment is, for example, generally used to increase the range or distance of a human powered effort in comparison to the unassisted range or distance. Exoskeletons may also be composed of more than one assistive power source combined with the human power.

For the sake of simplicity, any power source, other than human, will be hereinafter referred to as assistive power source.

Usually, exoskeletons or human hybrid powertrains include gearing or clutch systems, designed to effectively combine the assistive power source to the human power source, in order to provide an integrated system. In simple exoskeletons, the assistive power source is controlled by the human action and in more evolved exoskeletons, the assistive power source is controlled by a controller using data collected from sensors (including inertial measurement units). In some of the evolved exoskeletons, the controller can control the power output of the assistive power source as a function of the user needs or desires.

Electrical motors are easy to control because they may have higher bandwidth than other types of actuators. In electrical motor, where high dynamic response is sought, the most common form of electromechanical actuation is found in direct-drive motors, which may be prohibitively heavy for exoskeletons. Device weight can be considerably reduced by providing a reduction ratio between the motor and mechanical interfaces with the human. Indeed, when coupled to a speed reducer (e.g.: gearbox), electromechanical actuators are lighter and less expensive than direct drive solutions for a given torque output, but their higher output inertia, friction and backlash may diminish their dynamic performance. They may not be controlled with the same bandwidth. A good example would be a knee exoskeleton where a single electric motor and a speed reducer, such as a harmonic drive, are combined to provide a high torque-density actuator. However, the bandwidth of such actuator is comparatively lower than that of the electric motor or that of an electric motor of equivalent torque. The torque required to back-drive the exoskeleton may also be higher due to the friction of the gear system and the reflected inertia of the motor.

In the previous examples of a knee exoskeleton, if the user moves faster than the maximum speed of the actuator, the user will force against the exoskeleton. This situation may cause human injuries or discomfort due to low back-drivability. Such exoskeletons may be not easily controlled due to their low bandwidth and the user will feel engagement and disengagement of the assistive power source. Low bandwidth of the powertrain may be caused by the high inertia of parts that oppose to speed change in the system. When the user input speed varies, the high inertia of the system may be perceived or felt by the user and can become a nuisance or danger. A system with a low bandwidth may not adapt rapidly enough to human muscular dynamics such that the user may feel connected to a mechanical device that may cause an adaptation delay. The nuisance may come from the fact that the mechanical system speed is not able to follow the user's input speed, creating sticking points or unnatural movement. Higher bandwidth would make the system more transparent to the user. For example, if someone wants a device to apply a proportional assistance to the user's applied force in order to create the illusion of ease in moving loads, but the system has low bandwidth, the assistance will not adapt rapidly enough and will create a delay in the applied force that may be felt by the user. Usually, the bandwidth of an actuator may be reduced by inertial effects. For this reason, as the inertia increases, the actuator may lose its ability to adapt to the human change.

For controllability reasons, new technologies are needed in exoskeletons to match the impedance of assistive power sources with the impedance of the human. In such devices, where assistive power sources work in concert with the human and where smooth movement is sought, the technology used should have a bandwidth that may even be higher than the bandwidth of the human body part/joint that is assisted. The higher the bandwidth of the system contacting the human, the more transparent to the human the system will be and the more natural it will feel. When there is an unpredictable human power source in contact with the exoskeleton, the bandwidth of the assistive powertrain needs to match or exceed the bandwidth of the human, otherwise the controllability of the system may not be optimal. Also, the actuators assisting the human need to be compliant and easily back-drivable in order not to be damaged or to work well. A system in contact with the human body needs to be compliant so as not to expose the human body to unwanted forces or accelerations that could hurt the human or damage the actuator.

Other type of devices or equipment are recognised as providing human assistance similarly to exoskeletons, since they combine human power with the power of an additional source to assist the human. A good example of this is a prosthesis. In prostheses, a human is connected to the device that replaces a missing human limb. To reach smoother movement control, new technologies are needed, new technologies that would allow the admittance of the system to match or exceed the admittance of the human body. With such new technology, a device could also be paired with sensors that would help to identify the desired human force or movement and adjust the action of the prosthesis or exoskeleton to move in harmony with the human body.

SUMMARY

It is an aim of the present disclosure to provide a wearable device such as a prosthesis, orthosis or exoskeleton that employs an MR fluid actuator to connect the power of an assistive power source with the human power source.

It is also an aim of the present disclosure to present a wearable device having multiple MR fluid actuators selectively connecting a human power source or an assistive power source.

It is further an aim of the present disclosure to present a wearable device having an antagonist MR fluid actuator to reduce the induced torque generated by the powertrain to the human.

It is an additional aim of the present disclosure to present a wearable device having multiple MR fluid actuators selectively actuated by different MR fluid clutch apparatuses to create a multi degree-of-freedom actuated wearable device.

It is another aim of the present disclosure to present a wearable device that has a MR fluid actuator contributing to transform an output of a low bandwidth power source into a high bandwidth response.

Therefore, in accordance with a first embodiment of the present disclosure, there is provided a system comprising: at least one wearable device including a first body interface adapted to be secured to a first bodily part, at least a second body interface adapted to be secured to a second bodily part separated from the first bodily part by a physiological joint, at least one joint providing at least one degree of freedom between the first body interface and the second body interface; a magnetorheological (MR) fluid actuator unit comprising at least one power source, at least one MR fluid clutch apparatus receiving torque from the at least one power source, the at least one MR fluid clutch apparatus operable to generate a variable amount of torque transmission when subjected to a magnetic field; a transmission coupling the MR fluid actuator unit to the wearable device for converting torque from the MR fluid actuator unit to relative movement of the body interfaces with respect to one another.

Further in accordance with the first embodiment, the transmission includes for instance sets of a master cylinder and slave cylinder connected by a hydraulic circuit, the master cylinder being driven by the MR fluid actuator unit and driving the slave cylinder.

Still further in accordance with the first embodiment, the master cylinder is for instance connected to the at least one MR fluid clutch apparatus by one of a ball screw, rack and pinion and cable system.

Still further in accordance with the first embodiment, the slave cylinder is for instance mounted to the first body interface.

Still further in accordance with the first embodiment, the slave cylinder is for instance connected to second body interface by linkages.

Still further in accordance with the first embodiment, the linkages includes for instance a link connected to one of the body interface by at least one rotational joint and to another of the body interfaces by at least one translational joint.

Still further in accordance with the first embodiment, the slave cylinder pushes for instance on the link by rigid connection thereto.

Still further in accordance with the first embodiment, at least one of the master cylinder and the slave cylinder is for instance a rolling diaphragm cylinder.

Still further in accordance with the first embodiment, the MR fluid actuator unit has for instance at least a pair of the MR fluid clutch apparatus operated antagonistically for opposite movements of the first body interface relative to the second body interface.

Still further in accordance with the first embodiment, the MR fluid actuator unit has for instance at least one said MR fluid clutch apparatus operating antagonistically against a biasing member of the wearable device for opposite movements of the first body interface relative to the second body interface.

Still further in accordance with the first embodiment, the first body interface is for instance a shank body interface adapted to be secured to a shank of a user.

Still further in accordance with the first embodiment, the second body interface is for instance a foot body interface adapted to be secured to a foot or footwear of the user.

Still further in accordance with the first embodiment, a third body interface is for instance connected to the first body interface by one said joint, the third body interface being a thigh body interface adapted to be secured to a thigh of the user.

Still further in accordance with the first embodiment, the second body interface is for instance a thigh body interface adapted to be secured to a thigh of the user.

Still further in accordance with the first embodiment, two of the wearable device are for instance provided, with one said wearable device being a right leg exoskeleton, and one said wearable device being a left leg exoskeleton.

Still further in accordance with the first embodiment, the first body interface is for instance an upper arm body interface adapted to be secured to an upper arm of a user.

Still further in accordance with the first embodiment, the second body interface is for instance a lower arm interface adapted to be secured to a lower arm of the user.

Still further in accordance with the first embodiment, a third body interface is for instance connected to the first body interface by one said joint, the third body interface being a shoulder body interface adapted to be secured to a shoulder of the user.

Still further in accordance with the first embodiment, the second body interface is for instance a shoulder body interface adapted to be secured to a shoulder of the user.

Still further in accordance with the first embodiment, the at least one wearable device includes for instance at least one arm exoskeleton and at least one leg exoskeleton.

Still further in accordance with the first embodiment, the at least one power source is for instance an electric motor.

Still further in accordance with the first embodiment, the MR fluid actuator unit is located for instance remotely from the wearable device.

Still further in accordance with the first embodiment, the MR fluid actuator unit is for instance mounted on a dorsal support adapted to be worn by a user.

In accordance with a second embodiment of the present disclosure, there is provided a system comprising: at least one robotic arm including a chassis adapted to be supported by a user, an arm portion having a first member connected to the chassis by a first joint, at least a second member connected to the first member by a second joint, and an end effector at a free end of the arm portion; a magnetorheological (MR) fluid actuator unit comprising at least one power source, at least one MR fluid clutch apparatus receiving torque from the at least one power source, the at least one MR fluid clutch apparatus operable to generate a variable amount of torque transmission when subjected to a magnetic field; a transmission coupling the MR fluid actuator unit to the robotic arm for converting torque from the MR fluid actuator unit to relative movement of the members of the robotic arm with respect to one another and to the chassis.

Further in accordance with the second embodiment, the transmission includes for instance sets of a master cylinder and slave cylinder connected by a hydraulic circuit, the master cylinder being driven by the MR fluid actuator unit and driving the slave cylinder.

Still further in accordance with the second embodiment, the master cylinder is for instance connected to the at least one MR fluid clutch apparatus by one of a ball screw, rack and pinion and cable system.

Still further in accordance with the second embodiment, the slave cylinder is for instance mounted to the first member.

Still further in accordance with the second embodiment, the slave cylinder is for instance connected to second member by a cable and pulleys assembly.

Still further in accordance with the second embodiment, at least one of the master cylinder and the slave cylinder is for instance a rolling diaphragm cylinder.

Still further in accordance with the second embodiment, the MR fluid actuator unit has for instance at least a pair of the MR fluid clutch apparatus operated antagonistically for opposite movements of the members of the robotic arm with respect to one another and to the chassis.

Still further in accordance with the second embodiment, the MR fluid actuator unit has for instance at least one said MR fluid clutch apparatus operating antagonistically against a biasing member of the arm portion for opposite movements of the members of the robotic arm with respect to one another and to the chassis.

Still further in accordance with the second embodiment, the at least one power source is for instance an electric motor.

Still further in accordance with the second embodiment, the MR fluid actuator unit is for instance located remotely from the chassis.

Still further in accordance with the second embodiment, the chassis is for instance mounted on a dorsal support adapted to be worn by a user.

Still further in accordance with the second embodiment, the MR fluid actuator unit is for instance mounted on the chassis.

Still further in accordance with the second embodiment, the transmission includes for instance a cable transmission system, one end of a cable being driven by the MR fluid actuator unit and another end of the cable attached to the robotic arm.

In one embodiment, the wearable device includes for instance a human power source and assistive power source; a cable or hydraulic rolling diaphragm piston transmission connected to a final drive; and a selectively engageable magnetorheological fluid clutch (MRF) drivingly connected between the additional source and transmission device. An assistive power source may be operatively connected to the magnetorheological fluid clutch for selectively providing power to the wearable device via the magnetorheological fluid clutch, and in some configurations, to receive energy from the magnetorheological fluid clutch apparatus in braking or regenerative braking of the movement.

The wearable device may also include a controller/drive unit and energy storage device operatively connected to the assistive power source. The assistive power source may be operatively connected directly to the human power source and to the magnetorheological fluid clutch apparatus. Alternatively, the assistive power source is directly connected to the magnetorheological fluid clutch apparatus and operatively connected to the human power source by engagement of the magnetorheological fluid clutch apparatus.

The transmission may be a cable system or a hydraulic transmission or a combination of both.

The assistive power source may be connected to the input side or the output side of the magnetorheological fluid clutch apparatus.

These and other objects, features and advantages, according to the present invention, are provided by a wearable system including a frame or skeleton, user actuation means connected to the frame or skeleton for being engaged and moved by a user in order to provide human power to the wearable device, an additional source of power and MR fluid actuation means or a MR fluid actuator operatively connected in parallel to the human power input of the powertrain for applying controllable additional power to the system thereof. The MR fluid actuator unit may also be connected in series with the human power input in the case of a prosthesis. The MR fluid actuator preferably includes a MR fluid having a controllable apparent viscosity, a housing connected to the apparatus frame or skeleton and containing the MR fluid, and a rotary shaft extending outwardly from the housing and operatively connected between the MR fluid and the powertrain.

Control means, such as a microprocessor operating under a program control, is preferably operatively connected to the MR fluid force modulation means for causing a predetermined magnetic field strength to be applied to the MR fluid based upon a selected force modulation program that can consider information from sensors. Accordingly, a desired amount of force or power from the assistive power source can be provided to the powertrain in order to increase or decrease output of the powertrain during the wearable usage. The system may further comprise a sensor to measure the input of the human force or power to the system in order to control the output required by the assistive power source.

The wearable system may further comprise a display operatively connected to the control means. The control means may also include means for permitting the input of a program or of operating parameters. In addition, one or more sensors may be associated with the MR fluid force modulation means and connected to the control means for generating and displaying on the display the additional force or power provided by the additional source of power.

MR fluid actuators may be used on all kind of wearable systems, using various human input like the arms, hands, feet, legs or any other body part. Also, the powertrain can be used on various types of wearable system like exoskeletons, orthoses, body extensions, human controlled robot, only to name a few.

In complex exoskeletons or human controlled robots, the wearable powertrain may be used to move objects combining the human power with an assistive power source or power sources. Benefit and principles are the same as with wearable system. The objectives may still be to increase acceleration, improve control over the equipment or provide more force or power to the human operated equipment. An example of this is a working exoskeleton that may be used to support tools. The addition to a working exoskeleton of a MR fluid actuator connected to one of more body member would bring benefits. One or more sensors may be installed on the components and power sent to the members in proportion to the effort generated by the user, so that the user stays in control of the piece of equipment.

In other wearable devices, a robotic arm may be installed directly on a human. Manual labour is widely used in industrial sectors dealing with large assemblies such as aircrafts, ships, trains, heavy steel industry and the construction industry. The day-to-day tasks of assembly workers often require lifting heavy workpieces and work in non-ergonomic positions, such as raising arms for extended periods of time. Such conditions result in employee fatigue, increased risk of injury, and reduced production efficiency. A promising approach is to leverage the mobility and flexibility of human workers by augmenting their abilities with robotics technologies instead of trying to fully replace them. With wearable robots, the problem of accessing manufacturing sites is solved by using the mobility of human workers. Moreover, workers can direct in situ the work of the robots with no need for complex programming hence leading to increased versatility over traditional robotics. A wearable collaborative robotic tool (WCRT) to assist assembly workers may be used. With the high bandwidth of MR fluid actuation, this tool may filter human induced perturbations. As an example, assistance in gravity compensation, exerting a force on a surface or stabilising the position of an end effector in space may be achieved. These are only a few of the functions that the WCRT may assist in performing.

While supernumerary robotics arms are a promising new type of wearable robots, they also have challenges of their own. Since the robot is attached to the human, the robot must be able to accomplish its tasks despite disturbances due to the movement of the human. Accordingly, actuators capable of very fast motions are required while maintaining control of the output force, for instance to hold a panel in place. The robot must be lightweight in order not to impede the human worker. More specifically, the mass of the system must also be very close to the human body to avoid exhausting the human and be counter-productive.

Traditional electric motor actuation, results in a trade-off between speed and torque density. A robotic arm using direct-drive electric motors may have the capability of controlling its output force despite fast motion of the human base but may be heavy due to a poor force density. On the other hand, a robot using highly-geared motors may be too slow to compensate for motions of the human. While geared-motors used in conjunction with force sensors or elastic elements can be used to control of the output force in quasi-static situations, they remain a compromised solution with speed limitations and may not optimally maintain force control when the relative motion is too fast. Magnetorheological fluid actuators may offer good force fidelity for lightweight wearable actuation systems.

DESCRIPTION OF THE DRAWINGS

FIG. 10' is a schematic view of a MR fluid actuator unit using one of the MR fluid clutch apparatuses of FIG. 1, the MR fluid actuator used to decouple the motor and speed reducer from a Rotary-to-Rotary or Rotary-to-Linear converter;

FIG. 10" is a schematic view of a MR fluid actuator unit using one or more of the MR fluid clutch apparatuses of FIG. 1, all MR fluid actuators connected to the same speed reducer and actuating different Rotary-to-Rotary or Rotary-to-Linear converters;

DETAILED DESCRIPTION

Figure 1:
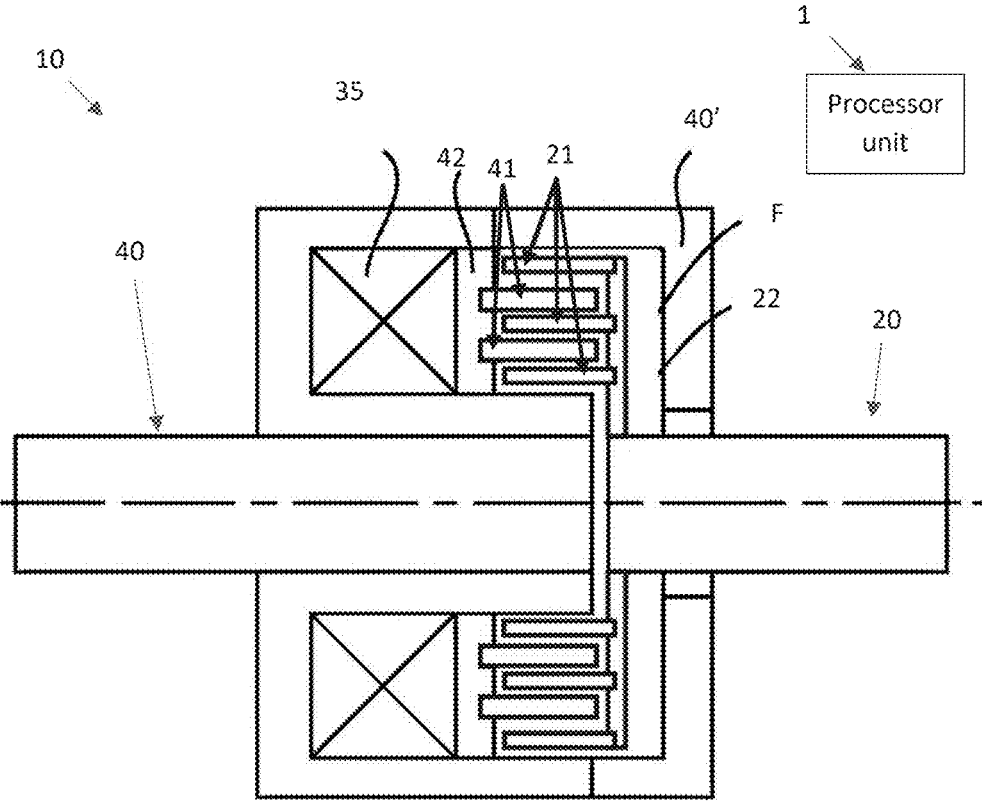
FIG. 1 is a schematic view of a generic magnetorheological (MR) fluid clutch apparatus, used by various embodiments of the present disclosure.

Referring to FIG. 1, there is illustrated a generic magnetorheological (MR) fluid clutch apparatus 10 configured to provide a mechanical output force based on a received input current provided by a processor unit 1 controlling the MR fluid clutch apparatus 10. The processor unit 1 is any type of electronic or electric device having controlling capability to control input current sent to the MR fluid clutch apparatus 10. In an embodiment, the processor unit 1 may receive signals from sensors, and compute data, for instance by way of firmware, to control the operation of the MR fluid clutch apparatus 10 based on settings, on requested assistance, etc, as will be explained hereinafter. The MR fluid clutch apparatus 10 has a driving member 20 with a disk 22 from which project drums 21 in an axial direction, this assembly also known as input rotor 20. The MR fluid clutch apparatus 10 also has a driven member 40 with a disk 42 from which project drums 41 intertwined with the drums 21 to define an annular chamber(s) filled with an MR fluid F. The assembly of the driven member 40 and drums 41 is also known as the output rotor 40. The annular chamber is delimited by a casing 40' that is integral to the driven member 40, and thus some surfaces of the casing 40 opposite the drums 21 are known as shear surfaces as they will collaborate with the drums 21 during torque transmission, as described below. The driving member 20 may be an input shaft in mechanical communication with a power input, and driven member 40 may be in mechanical communication with a power output (i.e., force output, torque output). MR fluid F is a type of smart fluid that is composed of magnetisable particles disposed in a carrier fluid, usually a type of oil. When subjected to a magnetic field, the fluid may increase its apparent viscosity, potentially to the point of becoming a viscoplastic solid. The apparent viscosity is defined by the ratio between the operating shear stress and the operating shear rate of the MR fluid F comprised between opposite shear surfaces— i.e., that of the drums 21 on the driving side, and that of the drums 41 and of the shear surfaces of the casing 40' in the annular chamber. The magnetic field intensity mainly affects the yield shear stress of the MR fluid. The yield shear stress of the fluid when in its active ("on") state may be controlled by varying the magnetic field intensity produced by electromagnet 35 integrated in the casing 40', i.e., the input current, via the use of a controller such as the processor unit 1. Accordingly, the MR fluid's ability to transmit force can be controlled with the electromagnet 35, thereby acting as a clutch between the members 20 and 40. The electromagnet 35 is configured to vary the strength of the magnetic field such that the friction between the members 20 and 40 may be low enough to allow the driving member 20 to freely rotate with the driven member 40 and vice versa, i.e., in controlled slippage.

The driving member 20 is driven at a desired speed by a power source, like a rotary geared electric motor, and the output rotor is connected to a mechanical device to be controlled. The torque transmitted by the MR fluid clutch apparatus 10 is related to the intensity of the magnetic field passing through the MR fluid. The magnetic field intensity is modulated by a coil of the electromagnet 35, as controlled by the processor unit 1.

Figure 2:
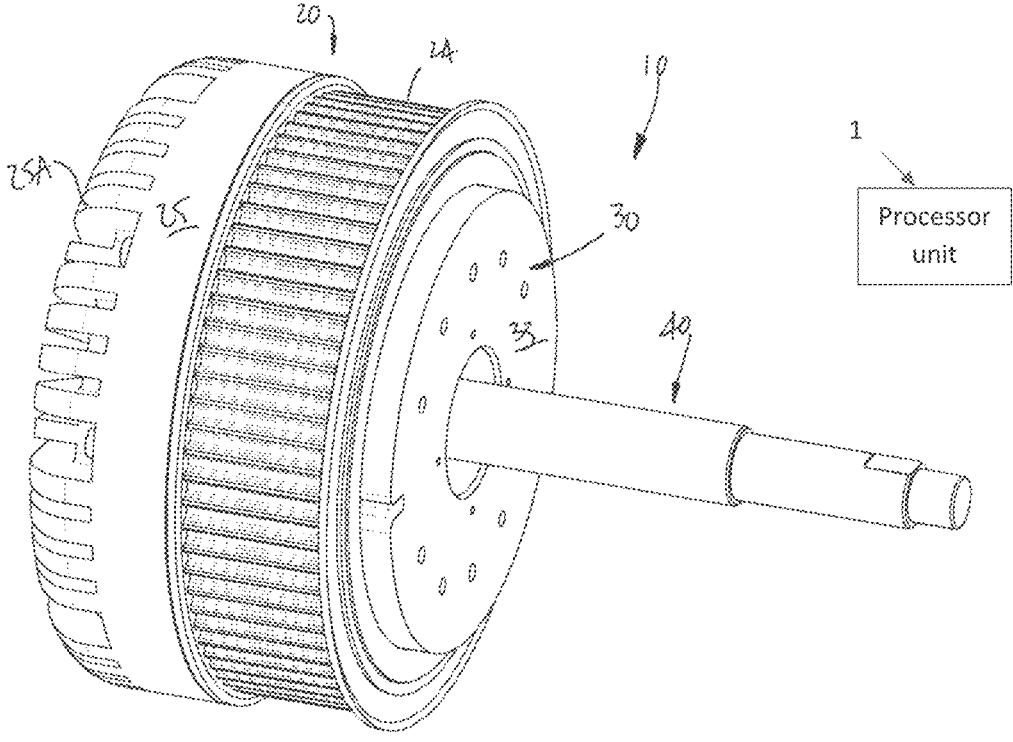
FIG. 2 is a perspective view of an MR fluid clutch apparatus of the present disclosure, as assembled.
Figure 3:
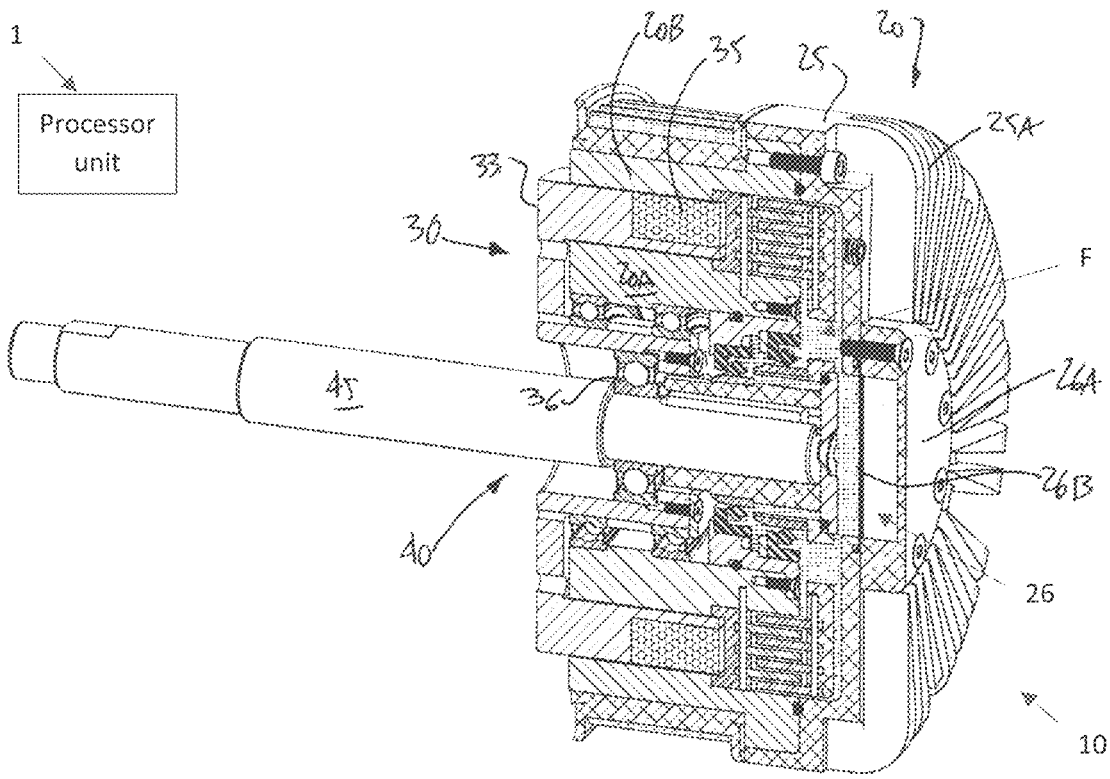
FIG. 3 is a partly sectioned view of the MR fluid clutch apparatus of FIG. 2.
Figure 4:
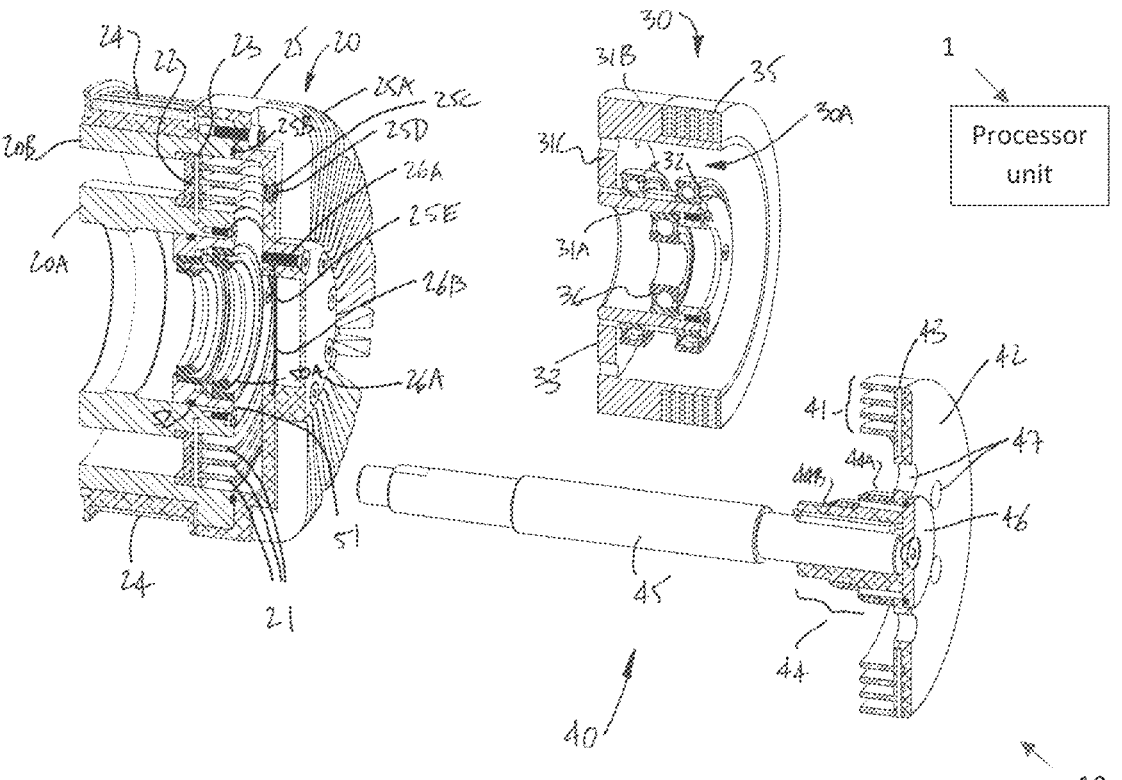
FIG. 4 is an exploded view of the MR fluid clutch apparatus of FIG. 2.

Referring to FIGS. 2, 3 and 4, the MR fluid clutch apparatus is generally shown at 10 as a whole. The MR fluid clutch apparatus 10 has similar components as the generic exemplary MR fluid clutch apparatus 10 of FIG. 1, whereby like reference numerals will refer to like components. The MR fluid clutch apparatus 10 has the input rotor 20, also known as the driving member, a stator 30 (including a coil), and the output rotor 40 also known as the driven member, and a MR fluid is located in an MR fluid chamber that is defined in the free space including the space between the drums of the rotor 20 and the rotor 40.

The input rotor 20 may be driven at a constant or variable speed prescribed by a rotary power source, not shown, like a rotary internal combustion engine or electric motor. The output rotor 40 is connected to a mechanical output, not shown, to be controlled. When a current circulates in the coil 35 of the stator 30, a magnetic field is induced in the stator 30 and passes through the drums and the MR fluid F. Then, a torque, dependent on the magnetic field intensity, is transmitted from the input rotor 20 to the output rotor 40 by shearing the MR fluid F in between the drums. Although the description that follows indicates that the rotor 20 is the input rotor and the rotor 40 is the output rotor, it is pointed out that the rotor 20 could be the output rotor and the rotor

40 could be the input rotor. However, for the sake of clarity and simplicity and to avoid unnecessary redundancy, the description will pursue with "input rotor 20" and "output rotor 40".

As best seen in FIGS. 3 and 4, the input rotor 20 has an inner magnetic core 20A and an outer magnetic core 20B, spaced apart from one another. The inner magnetic core 20A and outer magnetic core 20B are made of a ferromagnetic material that may have a high permeability, a high magnetization saturation, a high electrical resistivity and low hysteresis, such as silicon iron. Materials having a high electrical resistivity allow the magnetic field to establish faster by minimizing Eddy current and thus enhanced dynamic performance is achieved.

Cylindrical input drums 21 are secured to a drum holder 22 (also known as disc, plate, ring, etc), with the drum holder 22 spanning the radial space between the inner magnetic core 20A and the outer magnetic core 20B. In an embodiment, the drums 21 are in a tight-fit assembly in channels of the drum holder 22 and dowel pins 23 pass through all drums 21. The dowel pins 23 may also penetrate the inner magnetic core 20A, as shown in FIGS. 3 and 4. The drum holder 22 may consist of a non-ferromagnetic material to minimize the magnetic field passing through it and may also have a high electrical resistivity to minimize resistive loss during transient operation of the MR clutch apparatus 10.

In an example among many others, the input rotor 20 may be driven by a power source through a timing belt pulley, or any other driving member, like a chain sprocket, a gear, a flat belt pulley or a V-belt pulley. For illustrative purposes, a pulley portion 24 is provided for interconnection with a belt (not shown), the pulley portion 24 being a toothed pulley for cooperation with a timing belt (a.k.a., toothed, cog, synchronous belt). The pulley portion 24 may be tight-fitted or glued or positively locked to the outer magnetic core 20B, using mechanical fasteners, or the like.

A cover 25 is fixed to the outer magnetic core 20B, and in an embodiment made of aluminum for cooling purposes. Thermal fins 25A may be present on the cover 25 so that the MR fluid clutch apparatus 10 is cooled down by forced convection when the input rotor 20 rotates. The thermal fins 25A help to decrease the operating temperature of the MR fluid and may thus improve the life of the MR fluid clutch apparatus 10. The cover 25 may press a face static seal 25B onto the outer magnetic core 20B to prevent MR fluid leakage. Fill ports 25C may be defined through the cover 25, to fill the MR fluid clutch apparatus 10 with MR fluid. As illustrated, the fill ports 25C may be tapped and plugged using sealed set screws 25D among other solutions.

A central hole 25E in the cover 25 is closed by an expansion chamber cap 26A equipped with a flexible membrane 26B to allow MR fluid expansion during either temperature increase or MR fluid phase transition when aged. To counter the bulging of the membrane 26B due to the MR fluid, some compliant material, such as polyurethane foam, may be placed in the empty expansion volume between the expansion chamber cap 26A and the flexible membrane 26B. The compliant material therefore exerts a biasing pressure on the membrane 26B. Also, a vent hole may be present in the expansion chamber cap 26A to avoid excessive pressure build up in the empty expansion volume. Expansion chamber 26 may also be formed with a compressible material (e.g., closed cell neoprene) that may take less volume as the pressure increases in the MR Fluid F. If a compressible material is present, the expansion chamber may not need a vent hole and may not need a membrane 26B.

Still referring to FIGS. 3 and 4, the stator 30 is made of a ferromagnetic material to guide the magnetic field. The stator 30 may have an annular body with an annular cavity 30A formed in its U-shaped section. The inner magnetic core 20A is received in the annular cavity 30A, which may be defined by an inner annular wall 31A, an outer annular wall 31B, and a radial wall 31C, all of which may be a single monolithic piece. The inner magnetic core 20A is rotatably supported by one or more bearings 32, a pair being shown in FIGS. 3 and 4. Although the bearings 32 are shown located between the inner magnetic core 20A and the stator 30, inward of the inner magnetic core 20A, it is considered to position the bearings 32 elsewhere, such as in radial fluid gaps described below. The stator 30 is for instance connected to a structure via bores on its outer face 33 (that is part of the radial wall 31C), and is thus the immovable component of the MR fluid clutch apparatus 10 relative to the structure.

Figure 5:
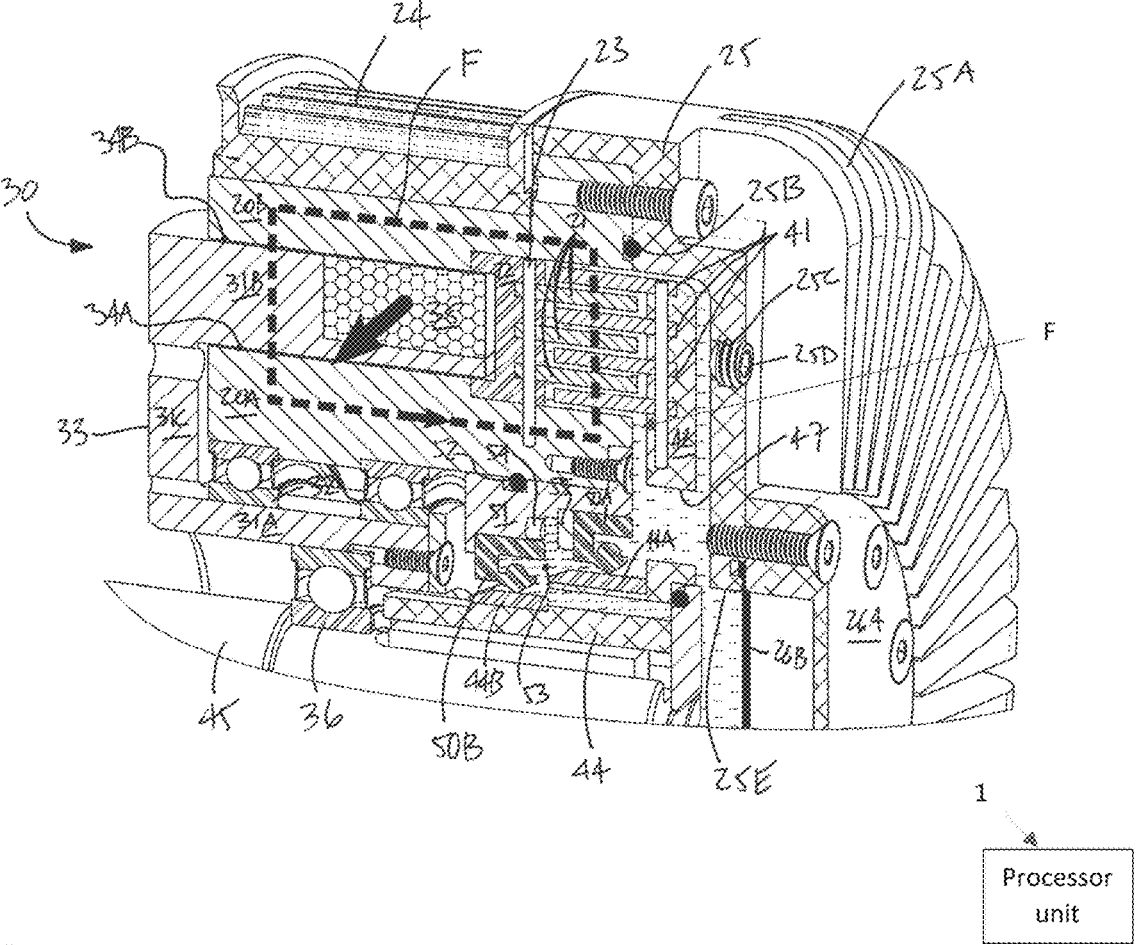
FIG. 5 is an enlarged view of the MR fluid clutch apparatus of FIG. 2, showing a magnetic field induced by a coil.

As best seen in FIG. 5, the stator 30 is sized such that radial fluid gaps 34A and 34B may be defined between the stator 30, and the inner magnetic core 20A and outer magnetic core 20B, respectively. The radial fluid gaps 34A and 34B, during use, are filled with a fluid, such as air and other gases, or lubricating and/or cooling liquids like oil, grease, etc. Hence, the radial fluid gaps 34A and 34B are free of solids during use. Coil 35 is secured to the annular body of the stator 30, for instance using an adhesive. It is contemplated to provide a slot through the stator 30 for passing wires connected to the coil 35, for powering the MR fluid clutch apparatus 10. The stator 30 further comprises one or more bearings 36 for rotatably supporting the output rotor 40, as described hereinafter.

The coil 35 may be wound using a high copper factor winding method. A higher copper ratio may lead to improved efficiency. Also considered are winding methods allowing flat wire winding, horizontal stacking, cylindrical stacking, for example. Multilayer PCBA winding is also considered (Heavy Copper PCBA) instead of copper only.

The bearings 32/36 are greased and may use no-contact seals to limit friction loss. The bearing arrangement featuring bearing(s) between the input rotor 20 and the stator 30, and separate bearing(s) between the stator 30 and the output rotor 40 enhances the safety of the MR fluid clutch apparatus 10. For example, if the input rotor 20 is jammed with the stator 30, the output rotor 40 is still free to rotate. Inversely, if the output rotor 40 is jammed with the stator 30, the power source that drives the input rotor 20 can still rotate.

The output rotor 40 has cylindrical output drums 41 that are secured to a drum holder 42 (e.g., plate, disc, etc) by a tight-fit assembly on the inner diameter of the drums 41. Dowel pins 43 may pass through the drums 41, among other ways to connect the output drums 41 to the drum holder 42. The output drums 41 are ferromagnetic so that the magnetic field easily passes through them (for example, with an equivalent magnetic flux in each of the drums). The drum holder 42 is made of a non-ferromagnetic material to minimize the magnetic field passing through it, like an aluminum alloy, to reduce the inertia of the output rotor 40.

The drum holder 42 has a shaft interface 44 by which it is connected to a shaft 45. In an embodiment, the shaft interface 44 is a sleeve-like component that is rotationally coupled to the shaft 45, and may have wear sleeves 44A and 44B. The output rotor 40 is locked in rotation to the output shaft 45 by a key or any other locking device (splines, tight-fit, etc. . . . ). A sealed shaft cap 46 is used to axially maintain the output rotor 40 relatively to the output shaft 45 and to prevent MR fluid leakage. A flat portion for a key may be defined on the output shaft 45 to ease screwing the shaft cap 46. This arrangement is one among others to connect the drum holder 42 to the shaft 45, such that the shaft 45 may receive the driving actuation from the input rotor 20 via the drum holder 42. The drum holder 22 further comprises throughbores 47 that may be circumferentially distributed therein to allow MR fluid circulation. As shown in FIGS. 3 and 4, the throughbores 47 are between the drums 41 and the shaft interface 44.

The MR fluid clutch apparatus 10 may use an odd number of drums 21 and 42, for example a mean value of about 7. More or fewer drums may be used according to the application. Using more than one drum helps to decrease the overall volume and weight of the MR fluid clutch apparatus 10 for a given desired torque and a given diameter, as using multiple drums helps to reduce both the drum length and the cross-sections of the inner magnetic core 20A and the outer magnetic core 20B. In the same time, the time response of the magnetic circuit may be improved because the Eddy currents are minimized when the cross-sections of the magnetic cores are lower.

Referring to FIG. 5, the magnetic field F induced by the coil 35 follows a closed path which goes through the annular wall 31B of the stator 30, the radial fluid gap 34B, the outer magnetic core 20B, the MR fluid, the drums 21 and 41, the inner magnetic core 20A, and the radial fluid gap 34A. The radial fluid gaps 34A and 34B allow the coil 35 to be energized without the use of slip rings. In fact, the typical friction slip rings are replaced by magnetic slip rings performed by the two radial fluid gaps 34A and 34B. The radial fluid gaps 34A and 34B are radial rather than axial for two reasons. Firstly, radial tolerance is readily reached so that the fluid gaps can be quite small (<0.2 mm) and thus the additional number of turns in the coil required to magnetize the fluid gaps 34A and 34B is minimized. Secondly, the magnetic attractive force in the fluid gaps 34A and 34B between the stator 30 and both magnetic cores 20A and 20B is nearly cancelled due to the rotational symmetry of the fluid gaps 34A and 34B. If the fluid gaps were axial, higher magnetic attractive forces would be present and would load the bearings axially.

Figure 6:
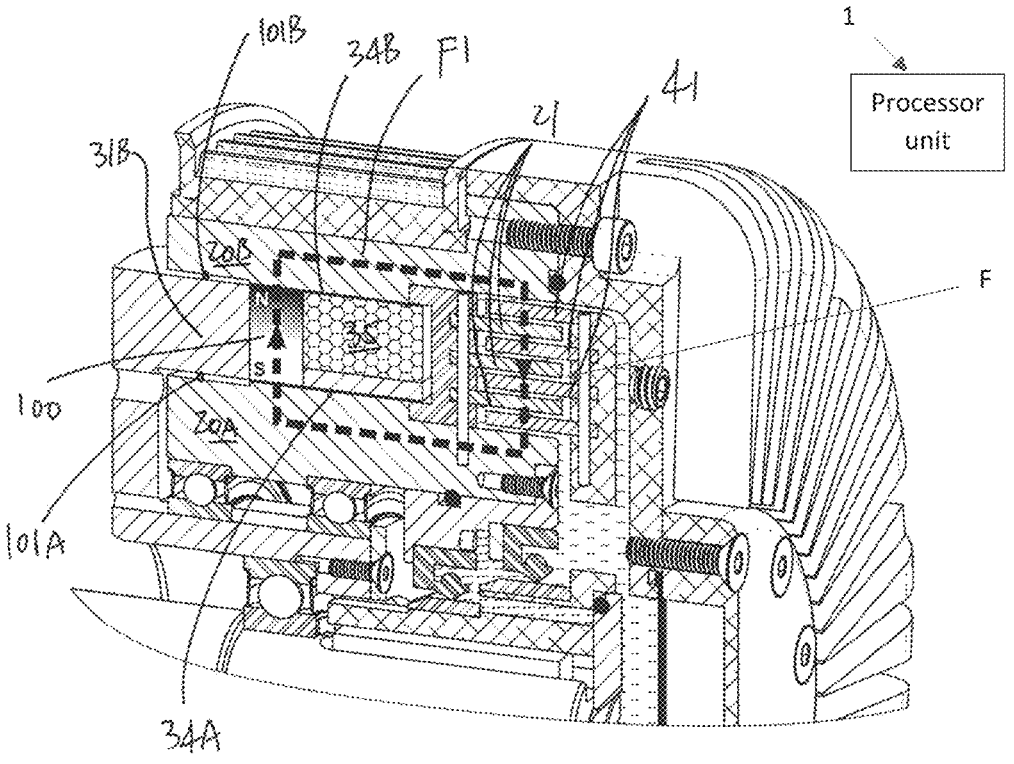
FIG. 6 is a partly sectioned view of the MR fluid clutch apparatus with a permanent magnet with a coil in an unpowered state, in accordance with the present disclosure.
Figure 7:
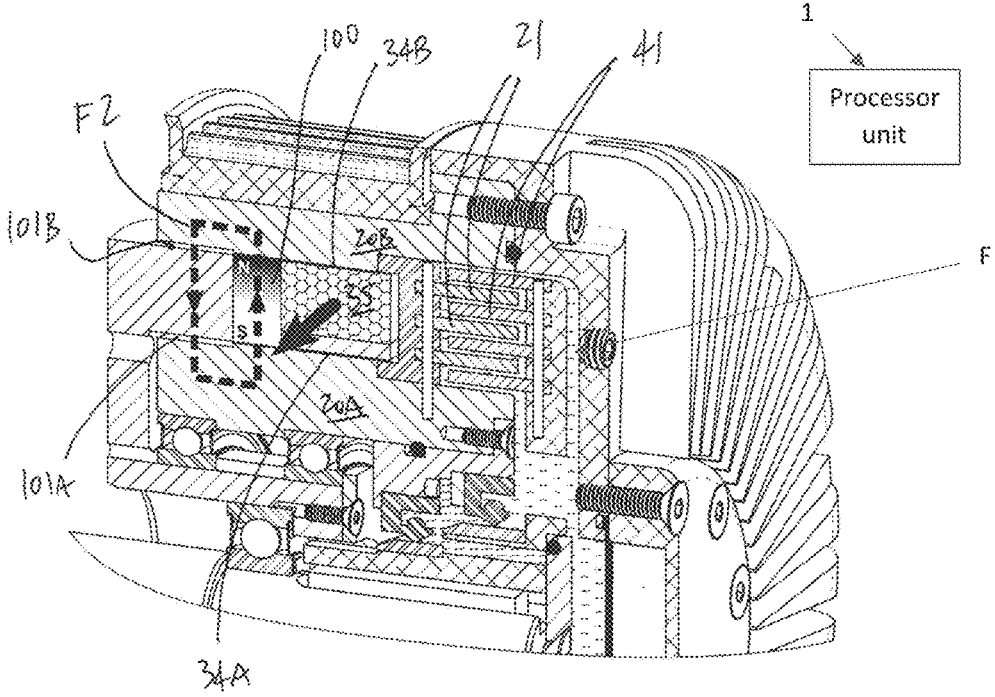
FIG. 7 is a partly sectioned view of the MR fluid clutch apparatus of FIG. 6, with the coil in a powered state.

Referring to FIGS. 6 and 7, the MR fluid clutch apparatus 10 is shown in yet another embodiment. The MR fluid clutch apparatus 10 of FIGS. 6 and 7 has numerous similar components with the MR fluid clutch apparatus 10 of FIGS. 3 to 6, whereby like elements will bear like numeral references, and their description is not duplicated unnecessarily herein. A distinction lies in the presence of a permanent magnet 100 in the outer annular wall 31B, in addition to the coil 35.

As shown in FIG. 6, permanent magnet 100 is used to generate a magnetic field F1 in the MR fluid clutch apparatus 10 so that the apparatus 10 can transfer a constant output torque without the need to apply a current via the coil 35. The permanent magnet 100 is radially magnetized and may be a full solid annular part or an assembly of individual magnets (such as cylindrical magnets). Other radial fluid gaps 101A and 101B, "redirection gaps", separate the part of the annular wall 31B on the opposite side of the permanent magnet 100 than the coil 35, from the inner magnetic core 20A and the outer magnetic core 20B.

When no current is applied to the coil 35, as in FIG. 6, magnetic field F1 is present in the MR fluid according to the described magnetic flux path shown. Some magnetic flux circulates through the other radial fluid gaps 101A and 101B, separating the stator 30 from the inner magnetic core 20A and the outer magnetic core 20B. These gaps 101A and 101B are a bit wider than the gaps 34A and 34B, the width being in a radial direction. The width of the redirection gaps 101A and 101B controls the amount of magnetic flux desired in the MR fluid, a.k.a. the desired constant torque when no current is applied to coil 35. If the redirection gaps 101A and 101B are sufficiently wide, almost all the magnetic flux induced by the permanent magnet 100 goes through the MR fluid, leading to a high DC torque. If the redirection gaps 101A and 101B are radially narrower, the magnetic flux is shared between the MR fluid and the redirection gaps 101A and 101B, leading to a lower DC torque.

When a current is applied in the coil 35 according to the direction shown in FIG. 7 and the indicated polarity of the permanent magnet 100, the magnetic flux induced by the permanent magnet 100 is redirected in the redirection gaps 101A and 101B as shown by F2, which leads in a decrease of the torque of the MR fluid clutch apparatus 10. At a certain intensity of the coil current, the magnetic flux F1 in the MR fluid can be nearly cancelled and passed this intensity, it will increase again. The width of the redirection radial fluid gaps also controls the size of the winding of the coil 35. If the width is high, a bigger winding is required to redirect the magnetic flux.

If the current is applied in the reverse direction, the coil 35 assists the permanent magnet 100 in the generation of magnetic flux in the MR fluid, leading to the increase of the torque of the MR clutch apparatus 10.

Accordingly, the MR fluid clutch apparatus 10 has a normally "on state" for the MR fluid, because of the magnetic field induced by the permanent magnet 100. The coil 35 may then be powered to cause the MR fluid clutch apparatus 10 to reduce torque transmission and eventually be in an off state. This arrangement is useful for example when the MR fluid clutch apparatus 10 must maintain torque transmission in spite of a power outage. The magnetic field of the permanent magnet 100 would be of sufficient magnitude for the MR fluid clutch apparatus 10 to support a load without being powered.

Figure 8:
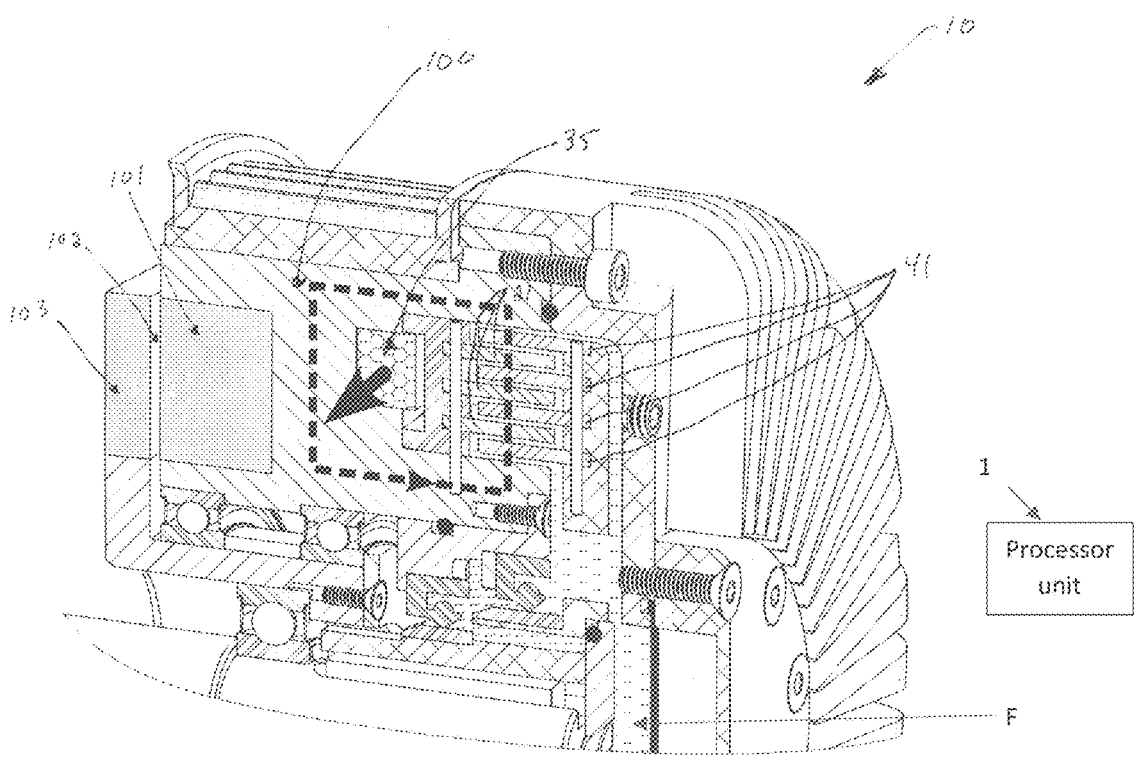
FIG. 8 is a schematic view of a generic MR fluid clutch apparatus, incorporating an axial fluid gap for power transmission.
Figure 9:
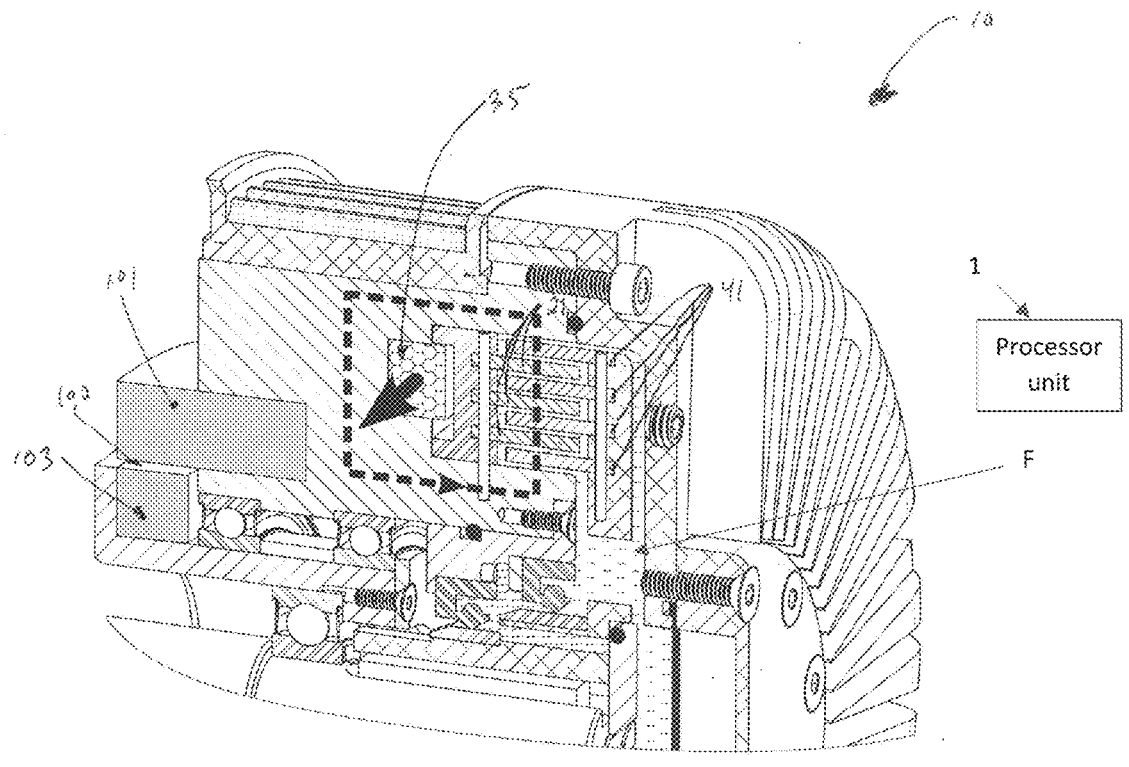
FIG. 9 is a schematic view of a MR fluid clutch apparatus, incorporating a radial fluid gap for power transmission.

As seen in FIG. 8, in an alternate construction of the clutch 10, the coil 35 of the clutch could be mounted on one of the rotating member of the clutch, here the magnetic core 100. The magnetic field F induced by the coil 35 follows a closed path which goes through the magnetic core 100, the MR fluid, the drums 21 and 41, the magnetic core 100. The coil 35 may be electrically linked to a power receiver 101 that is mounted on one the rotating part, here the magnetic core 100. An axial fluid gap 102 is provided between the power receiver 101 and a power emitter 103. The fluid gap or gaps 102 allow the power receiver 101 to be energized without the use of slip rings. In fact, the typical friction slip rings are replaced by contactless power slip ring or rings performed by the power emitter 103, the fluid gap 102 and the power receiver 101, allowing the clutch to do multiple turns. In FIG. 8, the fluid gap is axial (i.e., it lies in a plane to which the rotational axis is normal). As seen in FIG. 9, the fluid gap may be circumferential (it is annular in shape—a.k.a. radial fluid gap). In FIG. 9, the circumferential fluid gap 104 may separate the power emitter 103 and the power receiver 101.

In both FIG. 8 and FIG. 9, the contactless power emitter 103 may also receive signal or signals from the power receiver 101 and the power receiver 101 may transmit a signal or signals to the power emitter 103. The power receiver is then electrically linked to the coil 35 and to some sensor (not illustrated). The advantage of this contactless power transmission system is that the magnetic core reluctance is decreased by the elimination of the reluctance of the fluid gaps. Hence, power required in order to generate the equivalent magnetic flux in the MR fluid is reduced. The size of the coil 35 can then be reduced. The other advantage is that the heat dissipation in the coil 35 is also reduced, hence decreasing the cooling requirement of the clutch 10. An additional advantage is that the overall efficiency of the clutch is increased.

Figure 10:
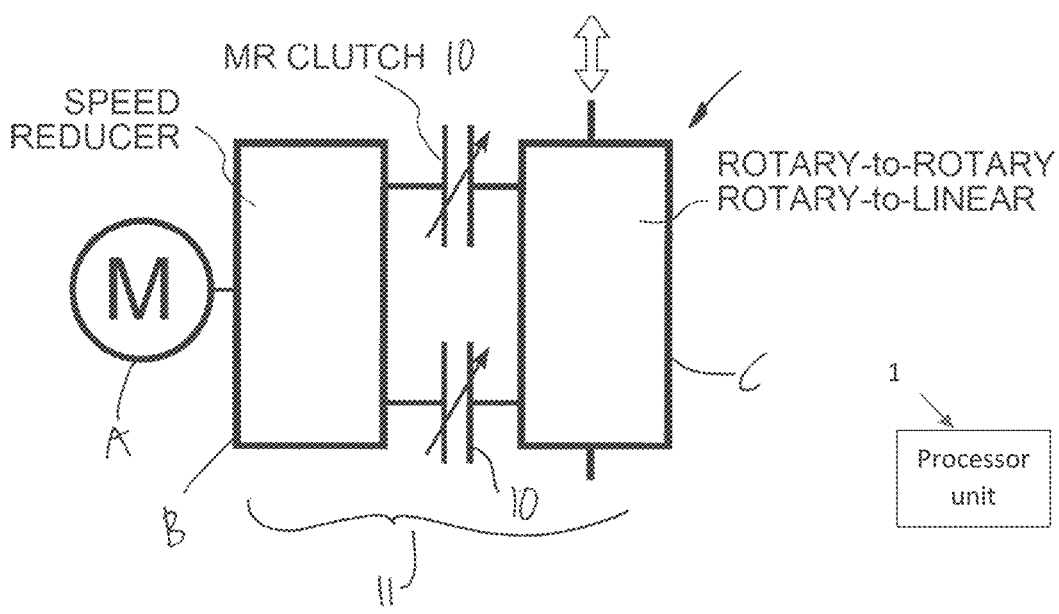
FIG. 10 is a schematic view of a MR fluid actuator unit using one or more of the MR fluid clutch apparatus of FIG. 1, both MR fluid clutch apparatuses connected to the speed reducer and turning in opposite direction.
Figure 10:
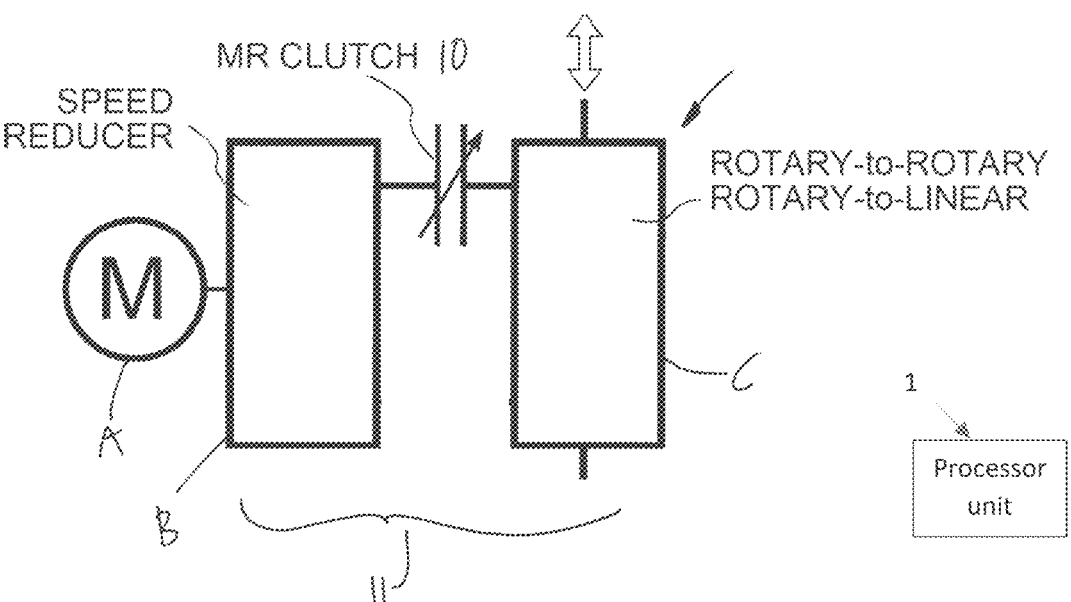

Referring to FIG. 10, the MR fluid actuator unit 11 is generally shown as being constituted of a power source A (e.g., a motor), a speed reducer B, at least one of the MR fluid clutch apparatuses 10 and an output device C or mechanism. The output device C may be a rotary-to-rotary device, or a rotary-to-linear device. In FIG. 10, the MR fluid actuator unit 11 has two MR fluid clutch apparatuses 10 turning in opposite directions. In this arrangement, when in off-state mode while the input shaft is turning, the viscous torque generated by the MR fluid clutch apparatuses 10 act in opposite direction thus they are not substantially transmitted to the output device C. The output of the rotary-to-rotary device, or a rotary-to-linear device may be controlled independently of the viscous torque generated in the MR fluid clutches apparatuses 10 when in off-state mode while the input shaft is turning by applying a force on either end of the converter.

Referring to FIG. 10', the MR fluid actuator unit 11 shown is similar to MR fluid actuator unit 11 of FIG. 10, with the difference that it is constituted of a single MR fluid clutch apparatus 10. In this configuration, the viscous torque may be transmitted to the rotary-to-rotary device or a rotary-to-linear device, slightly reducing the controllability of the system but decreasing the number of components required.

Referring to FIG. 10", the MR fluid actuator unit 11 shown is similar to the MR fluid actuator unit 11 of FIG. 10', with the difference that two or more MR fluid clutch apparatuses 10 are connected to the same speed reducer B, the two or more MR fluid clutch apparatuses 10 being connected to individual rotary-to-rotary device, or a rotary-to-linear device. This arrangement may be useful to control individually a human-hybrid powertrain that has more than one output. This system may also include additional MR fluid clutch apparatuses (not shown) connected to one or more rotary-to-rotary or a rotary-to-linear device in order to increase the controllability of the associated rotary-to-rotary or a rotary-to-linear device, as explained in FIG. 10.

Figure 11:
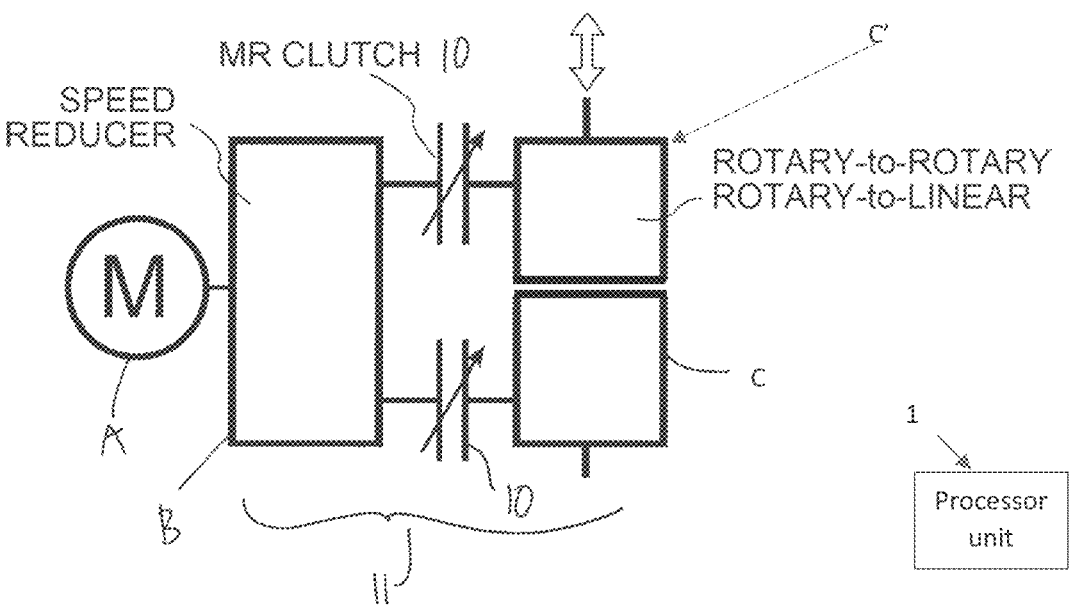
FIG. 11 is a schematic view of a MR fluid actuator unit using one or more of the MR fluid clutch apparatuses of FIG. 1, one of the MR fluid clutch connected to a fixed part and one MR fluid clutch connected to the speed reducer.
Figure 11:
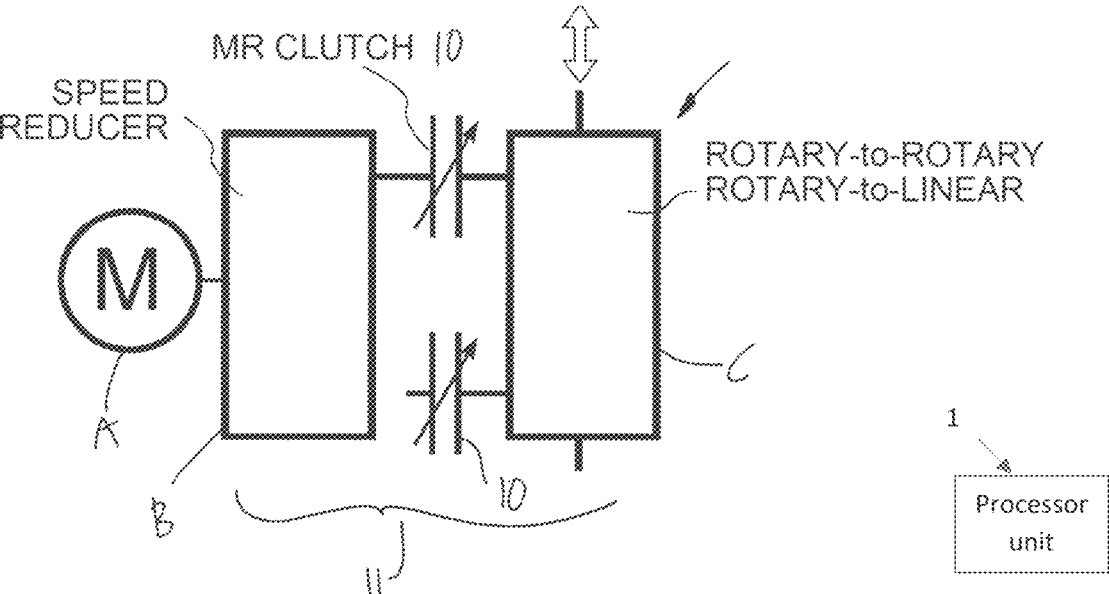

Referring to FIG. 11, an alternative construction of the MR fluid actuator 11 is shown, in which a single MR fluid clutch apparatus 10 is connected to the speed reducer and where a second MR fluid clutch apparatus 10 is connected to another component. This construction may be useful for the second clutch apparatus to reduce the effect on the output of the viscous torque generated by the first MR fluid clutch apparatus 10 that is connected to the speed reducer, increasing the controllability of the system.

Figure 12:
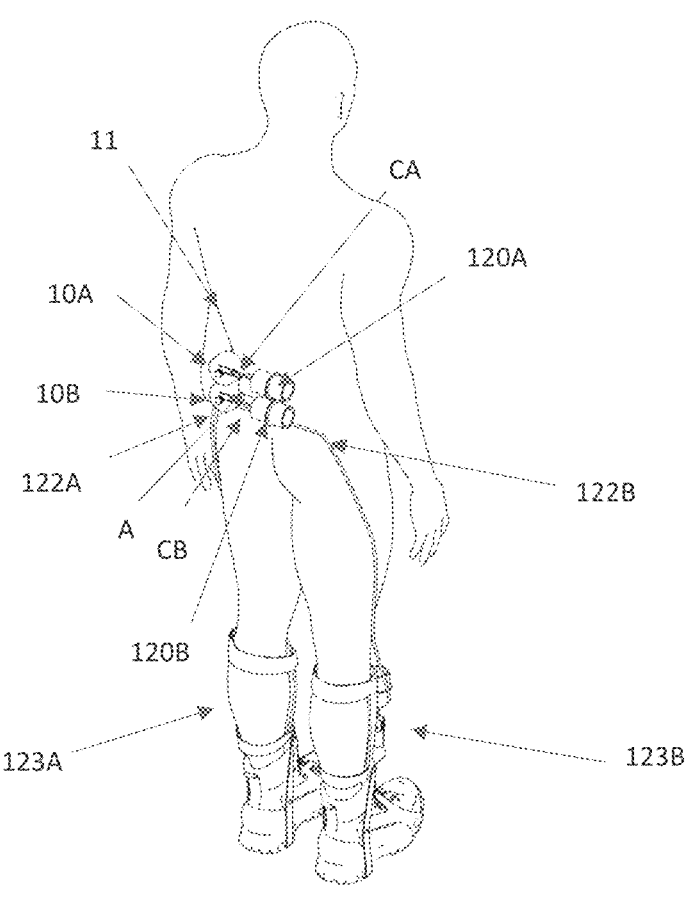
FIG. 12 is a perspective view of a pair of wearable devices sharing a power pack with a MR fluid actuator unit to modulate power sent from a motor and speed reducer to a human ankle exoskeleton.
Figure 13:
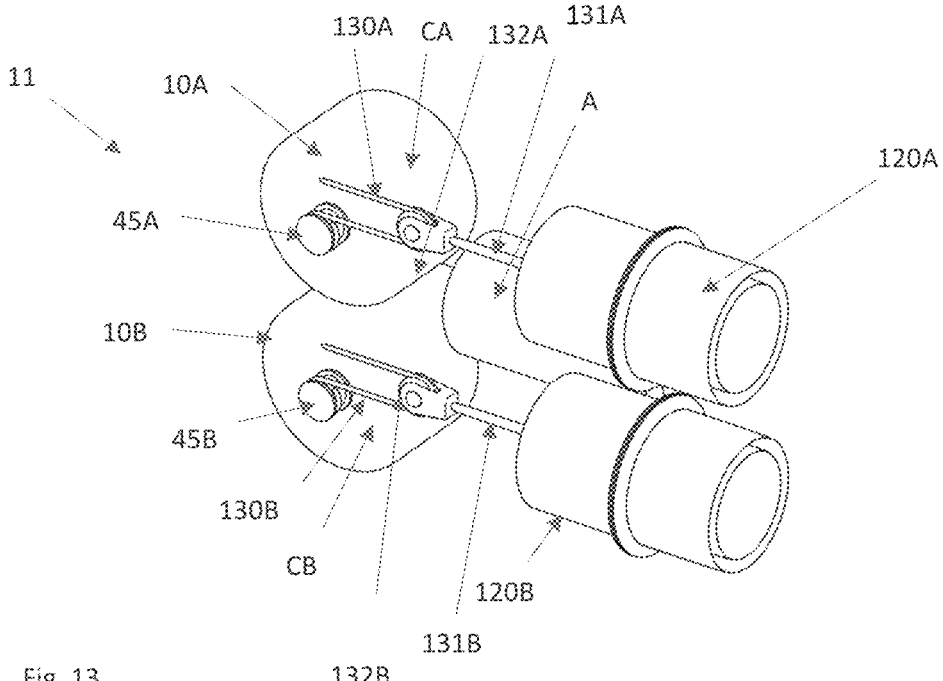
FIG. 13 is a perspective view of a master unit of the power pack powering the wearable devices of FIG. 12 including two MR fluid clutch apparatuses, actuating two different outputs.

Referring concurrently to FIGS. 12 and 13, a MR fluid actuator unit 11 is shown as operatively connected to a wearable device. While the expression "wearable device" is used for consistency, other expressions may be used to describe the wearable device, such as exoskeleton, orthosis, etc. The wearable device has a human-hybrid powertrain including the MR fluid actuator unit 11. The MR fluid actuator unit 11 may include a power source A (e.g., a motor), a speed reducer B, at least one of the MR fluid clutch apparatuses 10 and an output device CA, CB or mechanism. In the shown example, the speed reducer is connected to the MR fluid clutch apparatuses 10A and 10B (e.g., to their cover 25) and the output shaft 45A and 45B are connected to the output devices CA and CB, respectively, for example rotary-to-linear devices. The rotary-to-linear output devices CA and CB may be connected to master cylinders 120A and 120B or like transmission component (e.g., standard master cylinder, cable, Bowden cable, chain, etc) used to transmit forces. In the illustrated embodiment, the master cylinders 120A and 120B are rolling-diaphragm master cylinders used to transmit pressure and hence movement to hydraulic fluid present in hydraulic conduits 122A and 122B, respectively. Hydraulic conduits 122A and 122B are routed to reach respective remote wearable devices 123A and 123B that are attached to body limbs where actuation is required. Examples of wearable devices 123 are detailed in FIG. 14A and FIG. 14B. In the present embodiment, a single motor provides power for two individually controlled MR fluid clutch apparatuses 10A and 10B. This load sharing between two MR fluid clutches 10A and 10B may present the advantage of reducing the number of components and the weight of the MR fluid actuator unit 11. The load sharing is of particular advantage when power is to be sent alternatively to the remote wearable devices 123A and 123B at offset times (e.g., when a user is walking, power may need to be sent only to one ankle at a time).

FIG. 13 shows the MR actuator unit 11 in greater detail. The MR fluid actuator unit 11 that is illustrated is composed of a power source A (e.g., a motor), a speed reducer B (not shown), and two MR fluid clutch apparatuses, namely 10A and 10B. The speed reducer may be connected to the MR fluid clutch apparatuses 10A and 10B (e.g., to their cover 25) and the output shafts 45A and 45B are provided in this embodiment with cable pulleys, although the transmission component could be used (links and pivots, gear racks, ball screw, belts, linkages etc). Output shafts 45A and 45B are connected to cable 130A and 130B, respectively, that pull on piston rods 131A and 131B, respectively. In the present embodiment, a cable reduction ratio (e.g., 2:1) is provided by pulling on the cable 130 that has a fixed end (e.g. connected to the chassis or frame) and that pulls on returns pulleys 132A and 132B, respectively, attached to the piston rod 131A and 131B, respectively. Direct pulling and different reduction ratios are also possible. Hydraulic conduits 122A and 122B are connected to the master cylinders 120A and 120B, respectively. When a force is applied on piston rod 131A and 131B, pressure is built in the fluid in the master cylinders 120A and 120B, respectively, and fluid may be forced into the hydraulic conduits 122A and 122B, respectively.

Figure 14A:
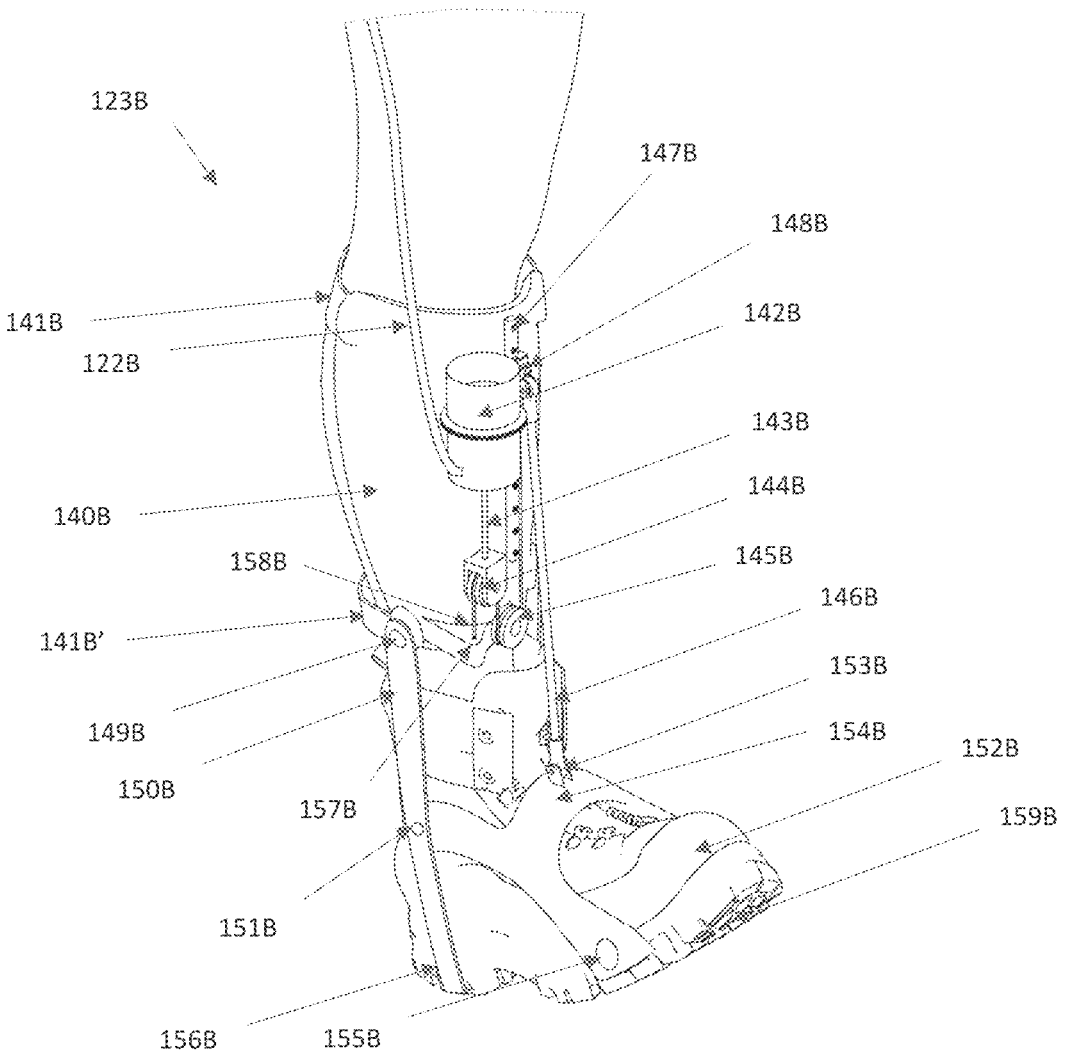
FIG. 14A is a perspective view of a slave unit on one of the wearable devices of FIG. 12 in its up position, including one hydraulic rolling diaphragm piston, actuating one output.
Figure 14B:
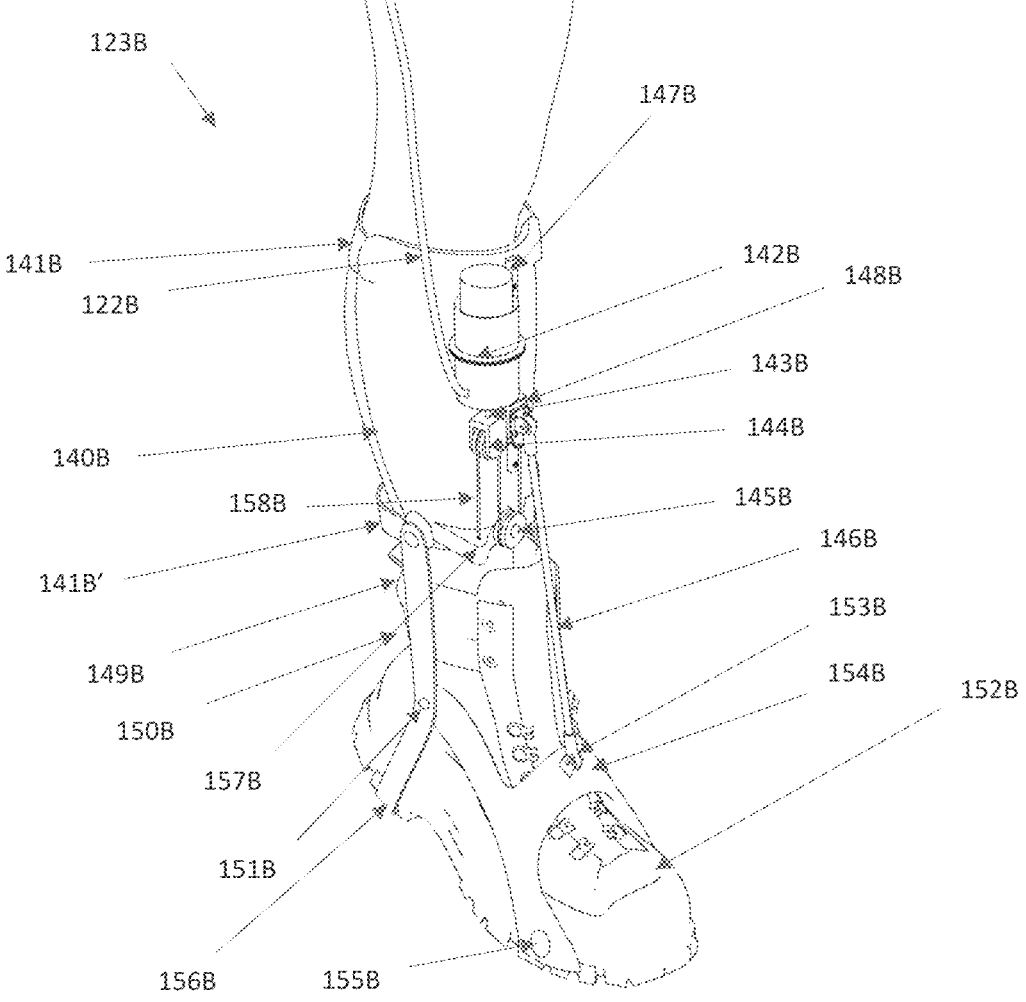
FIG. 14B is a perspective view of the slave unit of the wearable device of FIG. 12 in its down position, including one hydraulic rolling diaphragm piston, actuating one output.

FIGS. 14A and 14B show the wearable device 123B in greater detail, and may be a mirror image of wearable device 123A. For simplicity, only one of the wearable devices 123 is shown. The wearable device 123B is an ankle exoskeleton represented in a flexed position in FIG. 14A, and in an extended position in FIG. 14B. The wearable device 123B is composed of a first body interface 140B (e.g. shank pad) that is secured to the body using straps 141B and 141B'. This is one of numerous embodiments to secure non invasively a wearable device to a limb, in such a manner that the body interface 140B is generally immovable relative to a limb portion of the wearer. In the illustrated embodiment, the body interface 140B is secured to the tibia (lower leg). The expression "generally immovable" is used to illustrate that there may be negligible play as the body interface 140B and connectors 141B and 141B' are mounted to soft tissue. However, the mounting of the body interface 140B is such that the body interface 140B moves integrally with the limb portion (in this case, the lower leg). The body interface 140B may be a bar, a custom-fitted shell or sleeve, a brace, etc. Straps, strings, elastics, etc may be used as connectors 141B, 141B', if even necessary. Remote slave cylinder 142B is secured to the body interface 140B and connected to the hydraulic conduit 122B. When pressure builds in the master cylinder 120B, pressure is transmitted to the slave cylinder 142B via the hydraulic conduit 122B. Pressure in the slave cylinder 142B creates a force on piston rod 143B and a pulling action is generated at the pulley 144B attached to the piston rod 143B. Piston rod 143B pulls on a cable 158B. The cable 158B is routed from a fixed end 157B connected to the body interface 140B, to the pulley 144B attached to the piston rod 143B, to an idler pulley 145B attached to the body interface 140B, to a carriage 148B that may slide on a rail 147B. The pulling action on the piston rod 143B that is generated by the pressure in the slave piston 142B is hence transmitted to the carriage 148B. Force and movement of the carriage 148B is hence proportional to the force and movement generated by the piston rod 143B. In the shown embodiment, a 2:1 ratio is obtained and the force on the carriage 148B is one half of the force generated by the piston rod 143B, while the movement of the carriage 148B is twice the movement of the piston rod 143B. The 2:1 ratio is given as an example but other ratios are contemplated as a function of the anticipated use. The carriage 148B is connected to a push rod 146B using a swivel attachment (e.g. pivot, ball joint). The carriage system is shown as an example only, as other mechanisms (belt, chain, linkage, . . . ) may be used between the slave piston 142B and the push rod 146B. Moreover, the cable 158B may be routed to a second body interface 154B, if a pulling action is desired at the second body interface 154B. Also, the slave piston 142B may be mounted directly in series between a joint attached on the body interface 140B and the mounting point 153B if the slave piston 142B is of the push type. The push rod 146B transmits a force to a second body interface 154B through the mounting point 153B using a swivel attachment (e.g. ball joint, pivot, etc). In the shown embodiment, the second body interface 154B may be connected to a boot strap, a boot, a foot holder, etc. The second body interface 154B is relatively stiff so as to perform the function of transmitting the force generated at the mounting point 153B at a certain distance from the biological joint in order to generate a torque between the first body part (the lower leg) via the body interface 140B, and the second body part, the foot, via the body interface 154B. Second body interface 154B may be integrated to the boot structure. When force is transmitted in the push rod 146B, tension is generated on flexible tensioning members 150B and 150B' (not shown, on opposite side of on opposite side of the physiological joint) that link the first body interface 140B and the second body interface 154B. The flexible tensioning members 150B and 150B' (a.k.a., biasing member) may be in the form of a U-shaped structure connected at opposite end points to the body interface 140B by pivot joints 149B (and another similar joint on the opposite side). The tensioning members 150B and 150B' are said to be flexible, in that they can undergo elastic deformation during normal use in flexion or extension of the foot—it is compliant—, while still being stiff enough to transmit forces. Flexible tensioning members 150B and 150B' may include a hinge pivot formed by rotational joints 151B and 151B' (not shown, on the opposite side of on opposite side of the physiological joint) to allow angular movement between the first body interface 140B and the second body interface 154B. Flexible tensioning members 150B and 150B' are used in the described embodiment but rigid members may also be used. It may be contemplated to have the hinge points 151B and 151B' aligned with the physiological joint. Hinge points 151B and 151B' may or may not be attached to the boot 152B. When hinge points 151B and 151B' are attached to the boot 152B, it may not be necessary to have the portion 156B of the flexible tensioning members 150B and 150B' that goes under the heel as the force may be transmitted by the boot body itself, acting as the portion 156B. To generate a force between the two body interfaces 140B and 154B that will result in a torque generated at the hinge points 151B and 151B', the body interface 140B needs to be restrained to the user's body. The reaction force applied on the proximal body limb transversely to the longitudinal axis of the proximal body limb may be distributed by a pad between the body interface 140B and the proximal body limb. The reaction force applied on the proximal body limb along the longitudinal axis of the proximal body limb may be limited by the tensioning members 150B and 150B' that redirect the force under the heel and thus limit shear stress and friction between body interface 140B and the proximal body limb. This reaction force may also be redistributed in the straps 141B and 141B' by relying on friction and shear force between the body of the user and the body interface 140B, although this may be uncomfortable for the wearer. Friction and shear force on a user's body may be uncomfortable and could deter the user from using the wearable device. The force generated on the second body interface 154B may be transmitted directly to the user's distal body limb that is on the opposite side of the physiological joint (e.g. the foot in the illustrated embodiment), or to a part that may distribute the load on the distal body limb. The force generated on the second body interface may also applied in parallel to the distal body limb. In the present embodiment, to limit the force that the user's distal body limb has to transmit, the second body interface 154B is extended to transmit force directly to the ground or to a component of the boot 152B that is in contact with the ground (e.g. the sole for the boot 152B). To prevent undesired movement of the second body interface 154B in relation to the user, the second body interface 154B may be attached to the boot 152B using mounting points 155B on 155B' (not shown) on either sides of the boot 152B. The system may include a sensor 159B that measures the pressure, force or contact between the foot of the user and the ground or between the foot of the user and the boot. Other sensors (e.g. position, acceleration, force) may also be used. The illustrated system is one in which the force may only be applied in one direction. To compensate for this, a spring (not shown) or other biasing member may be added on the system to assist the foot in flexing when the MR fluid actuator unit 11 is not producing force. The MR fluid actuator unit 11 may then produce torque to eliminate the force produced by the spring and then both positive and negative torque may be produced at the ankle by using a single slave cylinder in each of the wearable devices 123A and 123B. A spring (not shown) or other biasing member may also be added on the system to force the foot in extension or to store energy caused by impact of the foot with the ground.

FIG. 14B shows the ankle exoskeleton of FIG. 14A in its extended position. In the illustrated examples of FIGS. 14A and 14B, a push rod 146B is installed on the front of the foot but other configurations are also considered. For example, a pulling action may be done at the back of the foot. This could imply that the tension members 150B and 150B' would transmit a compressive load. Tension member 150B and 150B' would need to be rigid or at least partially rigid between points 149B and 151B and between points 149B'

(not shown) and 151B' (not shown). The pulling action on the foot may be achieved by prolonging the rigid body interface 154B to the back of the foot and by having a pulling action between the first body interface 140B and the second body interface 154B. The pulling action may be realised using the same rolling-diaphragm piston system as the one shown in the previous embodiment, or achieved with a cable, ball-bearing cable or Bowden cable. The actuation of the rolling diaphragm, cable, ball-bearing cable or Bowden cable may be achieved remotely at the MR fluid actuator unit 11 or with a MR fluid actuator unit 11 located directly on the body part 140B or 154B. If the MR fluid actuator unit 11 is located remotely, i.e., at the leg, one component of the rolling-diaphragm piston system (e.g. the piston body) or one component of the Bowden cable (e.g. the cable liner) may be anchored on one body interface while the piston rod or cable is connected to the second body interface. Connection of the piston rod and cable may be achieved by using intermediate components or mechanisms. It is to be noted that body interface 140B is stand alone in FIGS. 12 to 14B but it is contemplated to link it to additional body members (e.g. a thigh body member). Also, additional body members may support components of the proposed system. Other body members may also be actuated in relation to one another in the manner shown in FIG. 18.

Stated differently, the wearable device 123 (i.e., 123B and 123B') are shown as being mounted to the lower leg to assist the extension movement of the foot about the ankle joint. A similar configuration could be used to assist the relative movement of other limb portions relative to a physiological joint, such as the upper leg (thigh/femur) vis à vis the lower leg (shank/tibia), about the knee joint, or such as the pelvis relative to the thigh/femur, via the hip joint. Upper body examples are provided above for the arms, but may even be extended to minute body parts, such as the fingers. The wearable devices 123 share a MR fluid actuator 11 that is part of a body-mounted power pack. This is a convenient positioning in the example of FIGS. 12 to 14B as the power pack provides assistance in alternance to the right leg and to the left leg, whereby the centralized positioning creates some symmetry to the system (e.g., a simplification in parts management, inventory, etc). For example, although not shown, the power pack may be on a backpack or like dorsal support, or on a hip pack. It is also contemplated to have the power pack on the floor or on an adjacent structure, for example when the user is standing still. Moreover, as mentioned above, the power pack may be mounted directly to the wearable device 123. Most embodiments shown use rotary-to-linear converters C, however, in some other human-hybrid powertrains, a rotary-to-rotary converter may be used. Rotary-to-rotary converters may be used in instances where the output force of the powertrain may have a rotary movement.

Figure 15A:
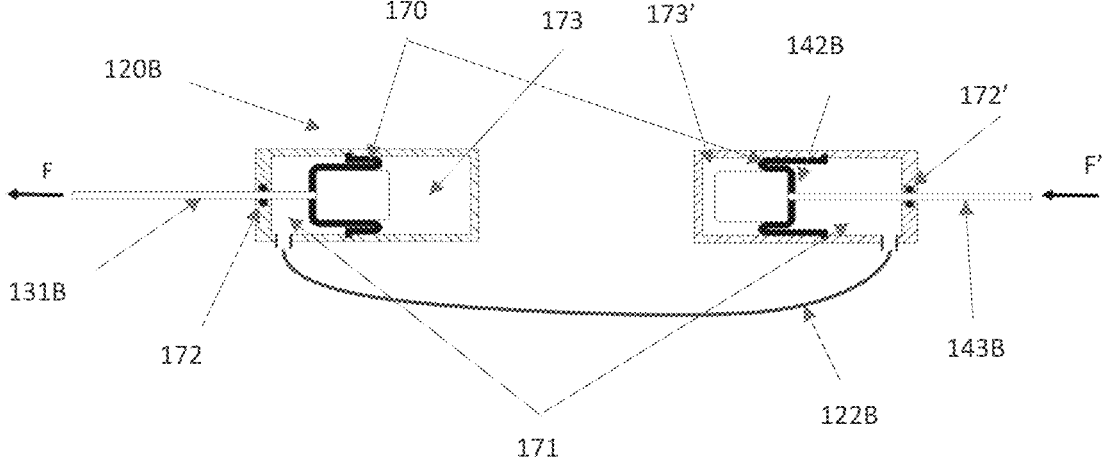
FIG. 15A is a perspective view of one possible transmission system used between the master unit and the slave unit of FIG. 12.

FIG. 15A is a schematic view of the fluid piston system that may be used in the embodiments of the present disclosure to transmit torque between the MR fluid actuator unit 11 and the wearable devices 123A and 123B. Other types of pistons may be used, though the proposed rolling-diaphragm piston is well suited for torque transmission in exoskeletons, such as the wearable devices 123A and 123B. In such systems, standard fluid pistons with sliding seals may present high static friction that may reduce the easiness of control of the wearable devices. In order to reduce the static friction forces, rolling-diaphragm pistons may be used. In such rolling-diaphragm pistons, the piston rod may work in compression (pushing action). Mechanisms (not shown) may be used to push the rolling-diaphragm piston but in some configurations in which cables may be used as rotary-to-translation converter (e.g. CA and CB of FIG. 13), it may be practical to have a rolling-diaphragm piston 120B used in tension (pulling action). The embodiment shown in FIG. 15A may have rolling-diaphragm pistons 120B and 142B that each incorporates a seal 172 and 172', respectively, on relatively small diameter pulling rods 131B and 143B, respectively. Bearings or bushings may be present to facilitate movement of rolling-diaphragm pistons 120B and 142B or pulling rods 131B and 143B. The relatively small section of the pulling rods 131B and 143B in relation to the effective diameter of the piston itself may reduce the magnitude of the static friction force of the piston. Reducing this static friction force may present a benefit for the control of the piston. The pulling force generated by the piston may be an order of magnitude superior to the static friction force generated at the seal of the piston rod and in some conditions the static friction force may be negligible, reducing the control complexity of the proposed exoskeleton system. The force applied to the pulling rod 131B may be transmitted to the pulling rod 143B with minimum force loss since the pressure of fluid 171 in the hydraulic circuit of both piston chambers of the rolling-diaphragm pistons 120B and 142B that are linked by the hydraulic conduit 122B is generally equal, the influence of the friction and static friction of rolling-diaphragm pistons 120B and 142B being negligible. To ensure optimal function, air in chamber 173 and 173' may be maintained at atmospheric pressure by having a vent (not shown) between chamber 173 and 173' connected to the outside. Chambers 173 and 173' may also be connected by an air conduit. Additional springs (not shown), mounted between pulling rods and rolling-diaphragm pistons frames may be used to always keep a minimal pressure in piston chambers and thus to avoid buckling of rolling diaphragms. An advantage of the proposed rolling-diaphragm piston system proposed is that a pressure sensor (not shown) may be installed in any piston chamber or in the hydraulic conduit 122B to monitor fluid pressure. Fluid pressure may be proportional to the force generated at the rolling-diaphragm slave cylinder. Pressure sensors may be cheaper than other types of force sensors. Position sensors may also be installed on the master cylinder 120 or on the slave cylinders 142 (whether or not they are rolling diaphragm) since the displacement of the master cylinder 120 may be proportional to the displacement on the slave cylinder 142. Other types of sensors may be used. With the high bandwidth of MR fluid clutch apparatuses 10, the force applied to the user's body may be achieved with high bandwidth. Applying the same principle to the position of the joint may also be possible by installing a position sensor on one of the piston rods 131B located near the MR fluid actuator unit 11. The position variation of the slave rod 143B may be obtained by measuring the position variation of rod 131B or other moving component located near the MR fluid actuator unit 11. The position may also be measured directly on the output pulley 45 of MR fluid clutch apparatus 10. By combining the remote force detection and remote position detection, non-collocated sensing is achieved, with sensing located remotely to the actuated joint, and this may present an advantage (i.e. wire management) and easiness of protection against impact or elements. Slave rolling diaphragm 142B may be replaced by a Mckibben muscle or other fluidic muscle. Rolling-diaphragm pistons 120B and 142B may also be replaced by other fluidic linear or rotary devices to transmit force between the MR fluid actuator unit 11 to the wearable device 123.

Figure 15B:
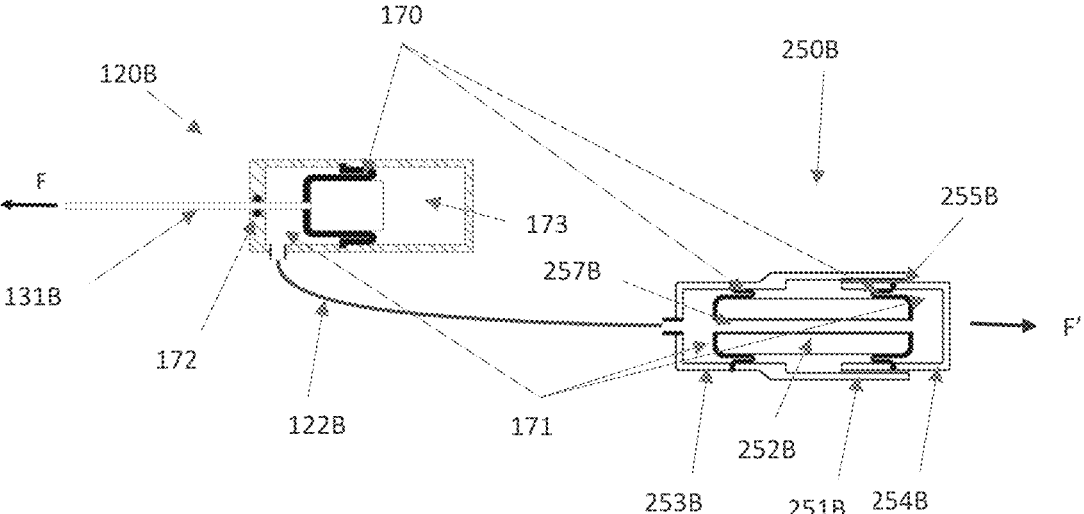
FIG. 15B is a perspective view of a similar transmission system as the one of FIG. 15A but with a dual hydraulic rolling diaphragm piston, actuating one output.

FIG. 15B shows a system similar to the one of FIG. 15A with the difference that the actuation is achieved with a dual rolling diaphragm piston 250B that pushes instead of pulling. The dual rolling diaphragm piston 250B may be mounted to push on a linkage. The body of the dual rolling diaphragm piston 250B is composed of two housings 253B and 254B that are linearly guided one in relation to the other by using linear bushings 255B that slide on guiding surface 251B that is attached to the housing 253B. Stated differently, a sliding joint is formed. Other guiding mechanisms may be used instead of the one proposed. A floating piston 252B is disposed in between the two housings 253B and 254B. The movement and force generated between the housing 253B and the floating piston 252B as well as the movement and force generated between the housing 254B and the floating piston 252B are transmitted to the mechanism. Since the shown configuration is a series arrangement, the forces in each body are hence equal and are the resulting force transmitted to the mechanism. Because of their nature, the rolling diaphragm pistons may be limited in travel, so the advantage of this series mounted rolling diaphragms piston may be that travel of the complete assembly may be greater than if a single rolling diaphragm piston were used. In order arrangement, system may be composed of piston system arranged in parallel and then the forces generated by the multiple pistons may add to be transmitted to the mechanism. The hydraulic fluid 171 enters the dual rolling diaphragm system by the inlet and occupies the inner cavity of the housing 253B and the 254B and also the fluid passage 257B linking the fluid zones of the housing 253B and the 254B. Each of the housing 253B and the 254B incorporate a rolling diaphragm 170. The rolling diaphragms 170 linking the housings 253B and the 254B and the floating piston 252B allow the two housings 253B and the 254B to distance one from the other by the cumulative displacement of each housing 253B and 254B in relation to the floating piston 257B. The pressure of the fluid 171 is roughly equal in each of the chambers of the housing 253B and the 254B and the fluid passage 257B. The dual rolling diaphragms piston 250B may also incorporate additional springs to maintain a minimal pressure in the fluid 171. These springs may link floating piston 152B to housings 253B and 254B respectively, or they may directly link housing 253B to housing 253B.

Figure 16:
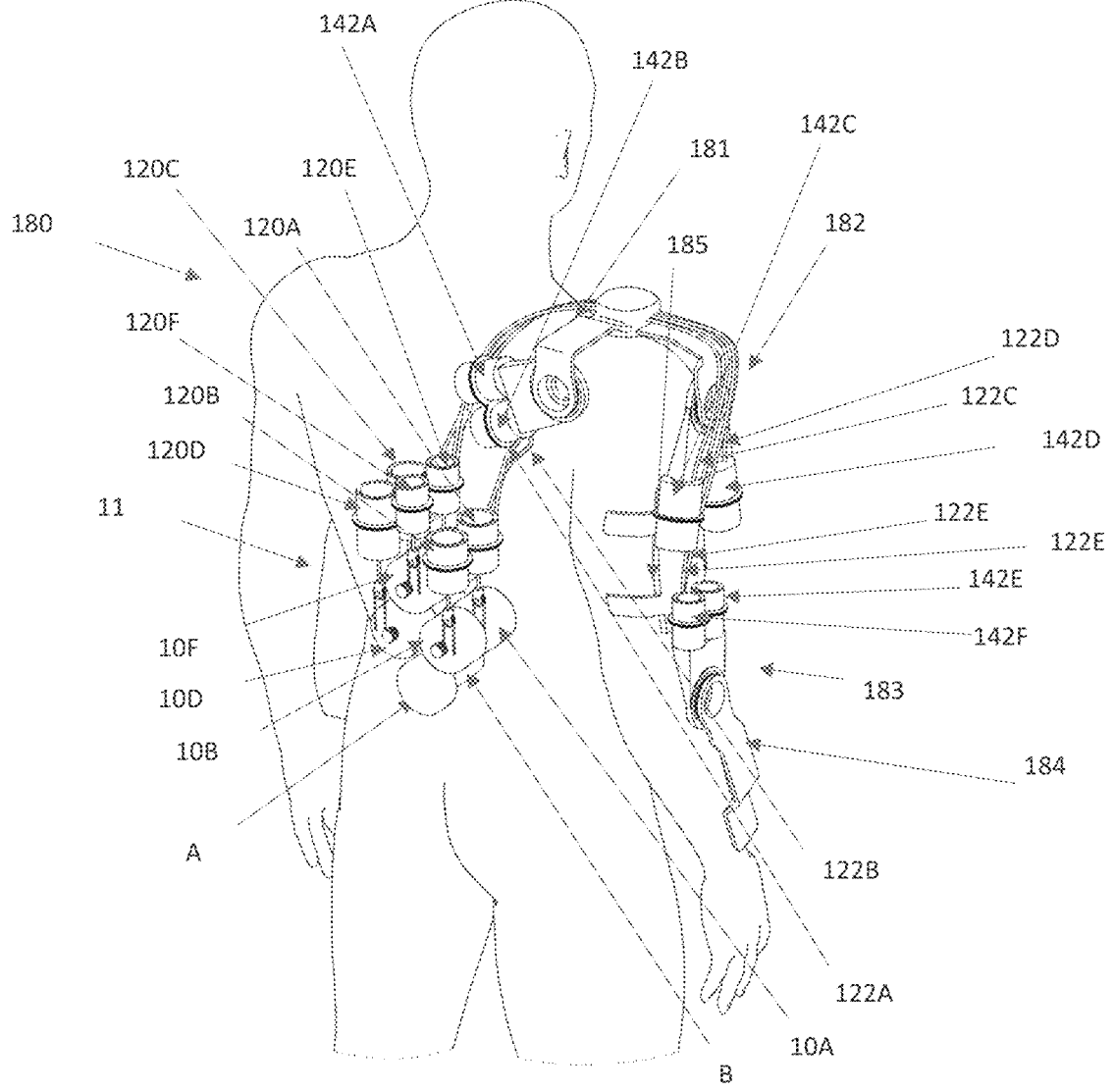
FIG. 16 is a perspective view of a wearable device using MR fluid actuators to modulate power sent from a high impedance motor and speed reducer to an upper body limb exoskeleton.

FIG. 16 shows another embodiment of a wearable device at 180. The wearable device 180 is an upper limb exoskeleton. Wearable device 180 is powered by a MR fluid actuator unit 11 that may be part of a user-supported power pack as in FIG. 16. The wearable device 180 may have remote actuated joints 181 and 182 at the shoulder and 183 at the elbow. The MR fluid actuator unit 11 is composed of a power source A (e.g., a single motor or more than one motor), a speed reducer B and six MR fluid clutch apparatuses 10A, 10B, 10C (not shown), 10D, 10E (not shown) and 10F (concurrently, the MR fluid clutch apparatuses 10). Each MR fluid clutch apparatus 10 is connected to a master cylinder 120, such as rolling-diaphragm cylinders. For ease of description, the master cylinders are referred to concurrently as 120, though they are shown as 120A, 120B, 120C, 120D, 120E and 120F and are respectively coupled to the MR fluid clutch apparatuses 10A, 10B, 10C, 10D, 10E and 10F (i.e., the corresponding affixed letters), with the same nomenclature applying to other components such as slave cylinders 142. Each of the master cylinders 120 is connected to a corresponding slave cylinders 142, such as rolling-diaphragm cylinders, using hydraulic conduits 122A, 122B, 122C, 122D, 122E and 122F (i.e., concurrently 122). For simplicity reasons, only joint 183 will be described here but joints 181 and 182 may operate in a similar manner. Body interface 184 may be attached on one body limb on one side of body articulation (e.g., the upper arm) and body interface 185 may be attached on the body limb (e.g., the lower arm) on the other side of the body articulation. To generate a torque in the joint 183 that may be aligned with the user's physiological joint, MR fluid actuator unit 11 may generate a force in master cylinders 120E or 120F in similar fashion as in FIG. 13. The pressure and movement generated in the master cylinder 120E or 120F is then transmitted to the slave cylinder 142E or 142F that may produce a torque between the body interfaces 183 and 184 in order to assist the user in performing some tasks. Although not shown, the body interfaces 183 and 184 may have any appropriate shape to be secured to the limbs for concurrent movement. This may include bars, braces, sleeves, straps, elastics, bands, harness. etc. The processor unit 1 may use readings from inertial measurement units to operate the arm exoskeleton 180.

Figure 17A:
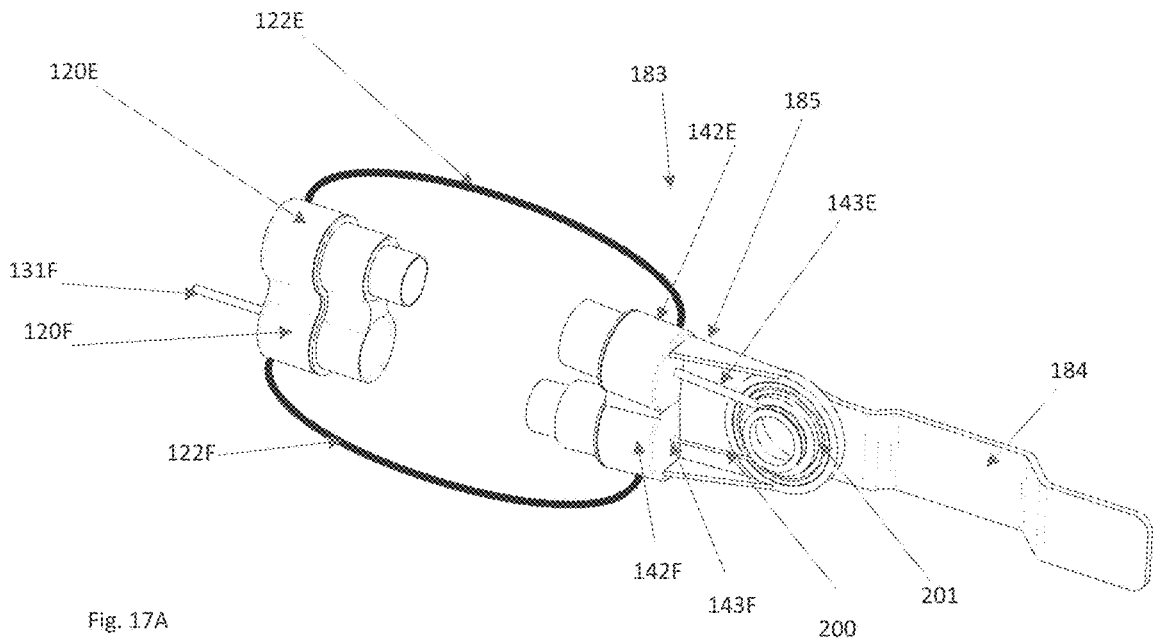
FIG. 17A is a perspective view of one possible transmission system used between the master unit and the slave unit of FIG. 16 where antagonist force actuation is performed by two hydraulic rolling diaphragm piston systems.
Figure 17B:
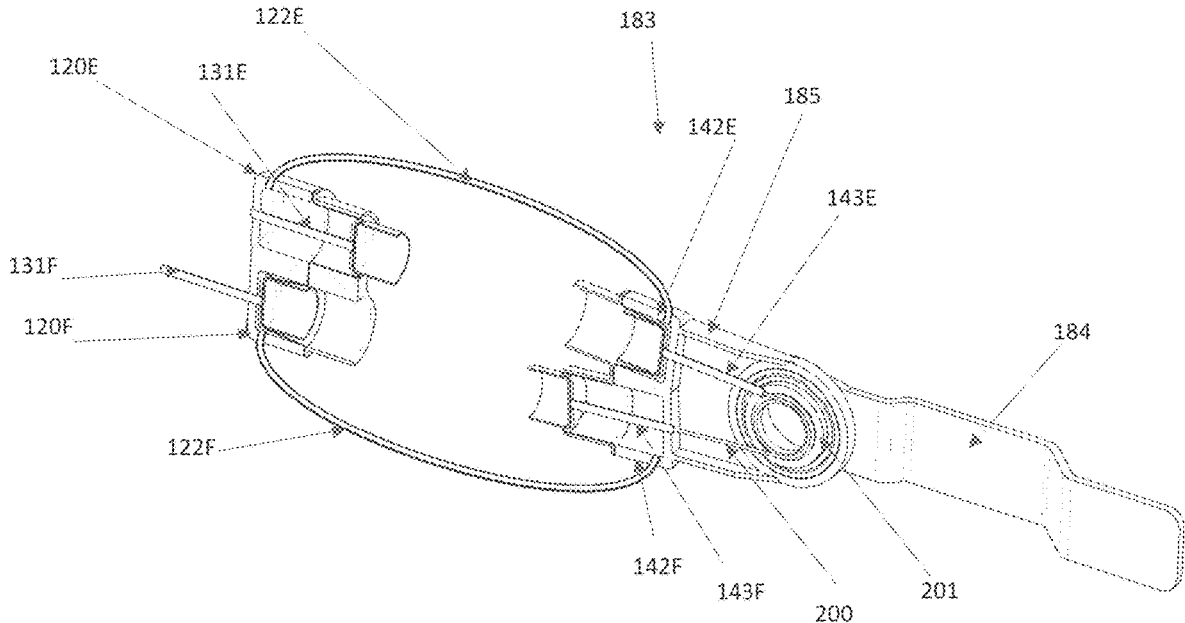
FIG. 17B is a sectional view of the transmission system of FIG. 17A.

A detailed description of the joint 183 is provided with reference to FIGS. 17A and 17B. FIG. 17A shows details of the joint 183 connected to the master cylinders 120E and 120F located in the MR fluid actuator unit 11. Slave cylinders 142E and 142F are connected to a linear-to-rotary converter composed of a cable 200 and a pulley 201. A bearing or bushing may be present to facilitate rotary movement of one body interface 185 in relation to the other body interface 184. In the shown example, the reciprocating movement of one of the piston rods 143E and 143F may pull on the cable 200 and control the rotation of body interface 184. In the shown embodiment, an antagonistic movement control is done due to the non-compressibility of the cable used in the concept. However, only one piston rod 143 may be used for both compression and tension forces if connected to a hard lever linear-to-rotary converter and if the piston is used is a two-way manner. For a two-way piston, two hydraulic conduits may be needed. Two-way pistons may also be used in the MR fluid actuator unit 11 provided the master cylinder piston rod is connected to two MR fluid clutch apparatuses 10 in order to maintain good bandwidth and controllability.

FIG. 17B shows a detailed longitudinal section of FIG. 17A. Rolling-diaphragms master cylinders 120E and 120F located at the MR fluid actuator unit 11 are shown in extreme positions and matching rolling-diaphragm slave cylinders 142E and 142F are shown in corresponding positions. Antagonistic movement of the interface 184 is shown in its corresponding position. To actuate the body interface 184 in CCW direction, MR fluid actuator unit 11 may actuate the MR fluid clutch apparatus 10E that may reel the cable 130E on the pulley 45E. Accordingly, the piston rod 131E will be pulled while increasing pressure in the rolling-diaphragm master cylinder 120E and will cause a flow of fluid 171. The pressure and fluid movement will be transferred by the hydraulic conduit 122E to the rolling diaphragm slave cylinder 142E and the piston rod 143E will apply a force and pull on the cable 200 that is attached to the pulley 201. The force and movement of the pulley 200 will be transferred in torque to the body interface 184. Torque generated between body interfaces 184 and 185 may generate a movement of body interface 184 in relation to body interface 185. With the high bandwidth of MR fluid clutch apparatus 10, the force applied to the body interface 184 may be achieved with high bandwidth.

Figure 18:
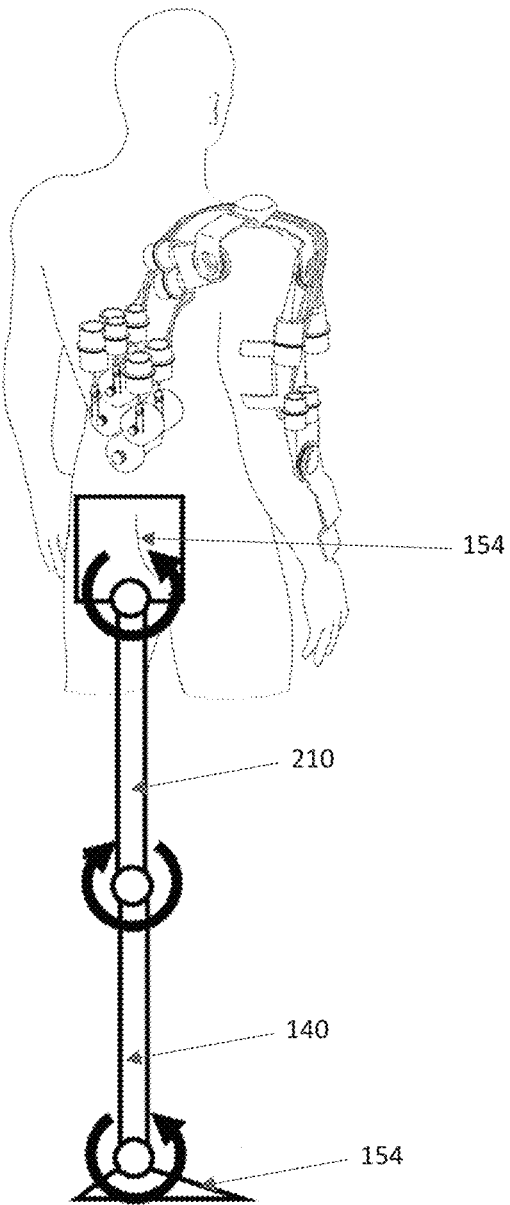
FIG. 18 is a schematic view of another embodiment of a wearable device comprising multiple degrees of freedom for upper and lower limbs.

FIG. 18 is a schematic view of another embodiment of a wearable device comprising multiple degrees of freedom for upper and lower limbs. It is to be noted that the movement of the body interface 154 may be actuated in relation to body interface 140 but also in relation to body member 210 provided a force may be applied between the two interfaces. Also, body interface 140 may be actuated in relation to body interface 210. Body interface 210 may be actuated in relation to body interface 154. The same principle applies to all other body parts. The MR fluid actuator unit 11 may be attached to any of the body interface or be located remotely (e.g. on a trolley or vehicle).

Figure 19:
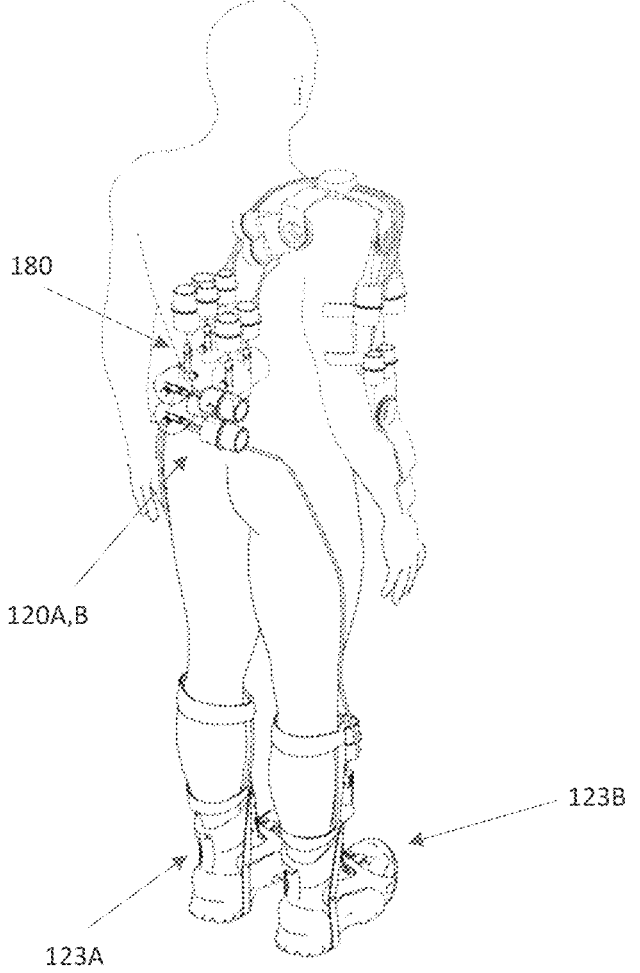
FIG. 19 is a perspective view of a wearable device using MR fluid actuators to modulate the power from a centralized motor and speed reducer to drive a human lower-limb exoskeleton as well as an upper body limb exoskeleton.

FIG. 19 is a schematic view of another embodiment of wearable devices comprising degrees of freedom from upper and lower limbs. Embodiments in accordance with the present disclosure may be comprised of independent or modular exoskeletons combined together. Embodiments in accordance with the present disclosure may rely on a common source of power for weight reduction. Embodiments in accordance with the present disclosure may rely on redundant or separate power source for reliability purposes.

Overall, the wearable devices proposed herein may be used to limit the human force required to move objects, or the force required in self displacement of the human (i.e., walking or running). The controllability of the wearable devices, because of the high bandwidth of MR fluid clutch apparatuses 10, may feel more natural than would a mechanical system with low bandwidth. It is to be noted that a single sensor or other types of sensors may be used. Also, motors A (not shown) may receive power from a battery 282 located close to the MR fluid actuator unit 11. For a device incorporating more multiple joints to actuate, it is possible to have only one motor A, distributing power and torque to one or multiple speed reducers C distributing power and torque to each rotary-to-rotary or rotary-to-linear converter.

Exoskeletons are described here but other types of wearable device (e.g. orthosis or prosthesis) may use similar arrangements as described above.

Although FIG. 16 to FIG. 17B show antagonist movements with two MR fluid clutches apparatuses 10 per joint, it is contemplated to have a single MR fluid clutch apparatus 10, with a biasing member or like force applying member providing and antagonistic force to enable a bi-directional output for the MR fluid clutch actuator unit 11, such as in FIGS. 12-14B. In some cases, gravity may be used as a biasing member. Human muscular force may also be used as a biasing member. In order to increase the safety of the device that applies a force on the user's body, additional sensors providing information about the environment or user may be used. For example, proximity sensor, vision sensor, contact sensor, may be used to decrease the chances of injuries. In the MR fluid actuator unit 11, other type of rotary-to-linear arrangements may be used. (i.e. a lead screw) and other types of tensioning devices may be used (i.e. chain, belt, hydraulic piston, etc. . . . ). In an embodiment, the wearable devices are connected to the MR fluid actuator(s) 11 by a cable and housing system instead of through hydraulics, for force transmission.

In the configurations of FIGS. 14A to 17B, the assembly may be reversed by mounting the MR fluid actuator unit 11 to the wearable devices while applying a force on the first part or the second part or by mounting the MR fluid actuator unit 11 directly on one of the body interfaces instead of having it remotely located.

In FIGS. 12 to 19, the MR fluid actuator unit 11 connected to body parts may be used to create virtual mechanical functions, such as damping, spring, vibration among others, generated by the MR fluid actuator unit 11. The virtual mechanical functions generated by the MR fluid actuator unit 11 may be programmable and adaptable to various conditions. Information about conditions may be provided by sensors.

In FIGS. 1 to 19, the magnetorheological fluid clutch apparatus 10 may selectively transmit a rotation force $F_{MR}$ to assist in displacing the load, via the proposed transmission systems (e.g.: capstan). This type of actuator may present advantages in some devices that may be actuated when powered since very low inertia and viscous force are generated when the MR fluid clutch apparatuses are not generating torque (e.g. when in OFF state). Also, cable reeling mechanism may be added at the actuator so if the actuated system 11 is used as part of a wearable and the actuator is forced to move by an outside force (i.e. a human) when the system is powered off, mechanism may "reel" the cable to prevent cable loosening situation on cable located in the MR actuator 11. The above example is one among other examples in which a tensioning mechanism may be integrated in a wearable and other tensioning mechanism that prevents cable loosening are considered. For example, when only cable end is present, a tensioning device (i.e. torsion spring only to name one) may act directly on the pulley 45 in order to prevent cable end loosening. Moreover, as an alternative to the pulleys 45, racks and pinions, chain and sprockets, hydraulics, pneumatics, etc, could be used as well.

Numerous other types of equipment using human-hybrid powertrain may also be adapted to use the MR fluid actuator unit 11 as described herein. Exoskeletons dedicated to rehabilitation or performance enhancement (such as in military environment or handling) may also use such wearable devices. A single/multiple power source connected to single/multiple speed reducers that drive MR clutch apparatuses may assist the human manipulations according to predetermined degrees of freedom. The high bandwidth of the proposed actuation may make the human movements feel natural while achieving displacements that may require less force than it would with sole human energy.

In all descriptions, there is illustrated one mechanical arrangement or MR fluid actuator configuration but other MR fluid actuators are considered. At least one MR fluid clutch apparatus is connected to a motor A or to a speed reducer B. Additional MR fluid clutch apparatuses may be connected to the motor A, to the speed reducer B, to the rotary-to-rotary or rotary-to-linear converter, or may be connected to any other parts or frame.

Figure 20A:
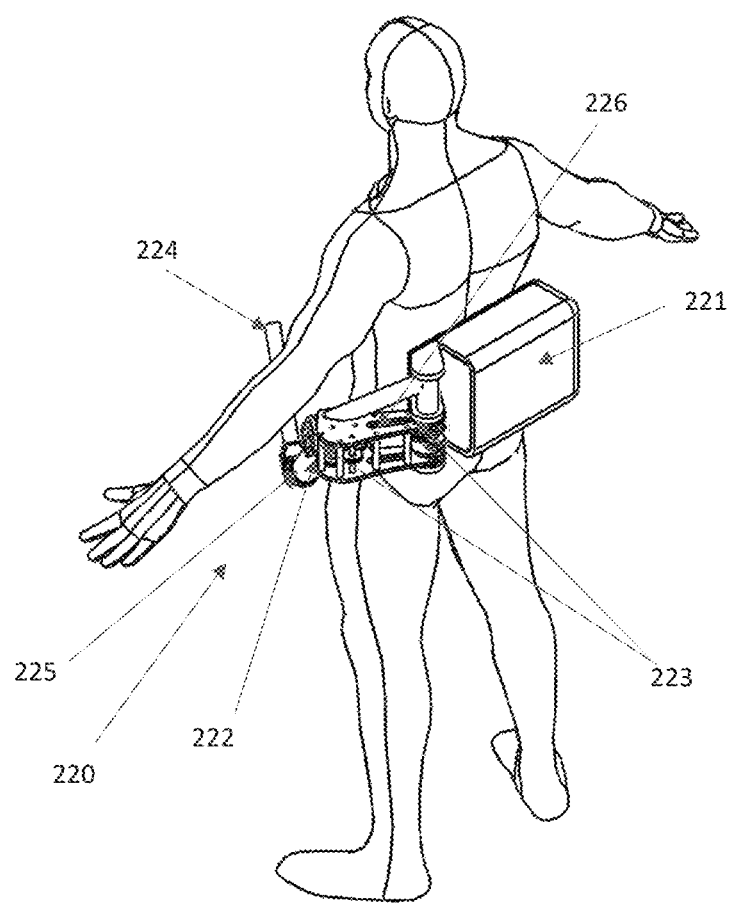
FIG. 20A is a perspective view of a wearable device using MR fluid actuators to drive a wearable robotic arm actuated with a cable system.
Figure 20B:
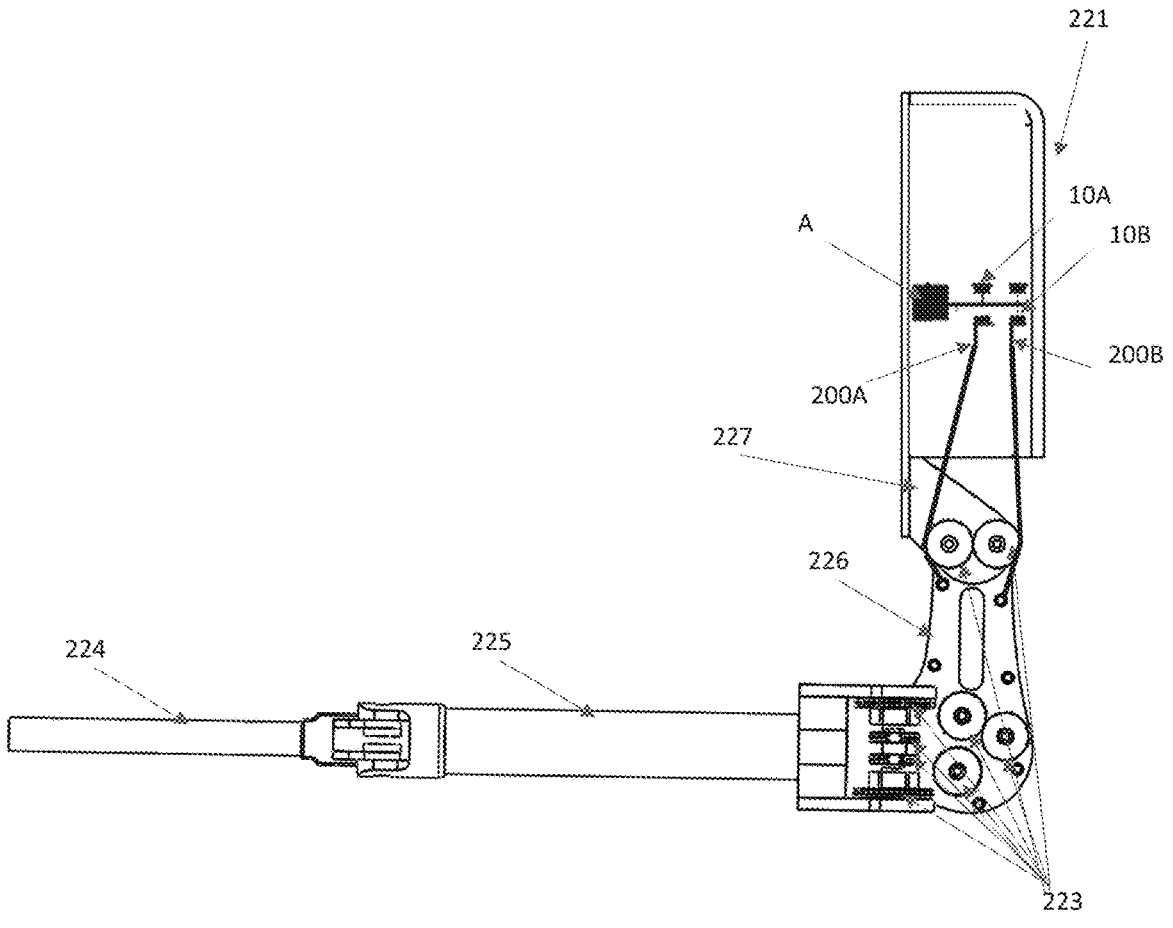
FIG. 20B is an elevation view of the robotic arm of FIG. 20A.

FIG. 20A shows a perspective view of a wearable robotic arm 220 that is attached to a human. The robotic arm 220 may have multiple actuated DOFs and the power unit 221 may also be supported by the human or by an adjacent structure, vehicle or ground. The robotic arm 220 illustrated is actuated by a cable system, although other types of transmissions may be used. Cables 222 are routed in the arm structure and guided by idler pulleys 223, or by cable housing. The power unit 221 may have a power source (i.e. motor), a reduction mechanism (i.e. a gearbox) and a pulley acting on one end of a cable connected to the joints of the robotic arm 220, actuating it with high bandwidth from MR fluid clutch apparatuses 10. The shown arm is a three DOF arm with an arm portion having members and an end effector, the arm portion connected to the chassis 227. A first member 226 is connected to the chassis 227 of the robotic arm 220 by a single DOF joint, the first member 226 also connected to second member 225 using another single DOF joint and then to an end effector 224. In the embodiment of FIGS. 20A and 20B, all the actuation of the DOF are performed using a cable system actuated by MR fluid clutch apparatuses 10 (not shown) that may be contained in a power unit 221. The processor unit 1 may use readings from inertial measurement units to operate the robotic arm 220.

In FIG. 20B, the cable actuation system is shown only for the first DOF for simplicity, with similar assemblies used for the other DOFs. A motor A is connected to MR fluid clutch apparatuses 10 in order to provide antagonistic actuation of the DOFs of the first member 226 that is linked to the chassis 227 (a.k.a., frame). One end of cable 200A may be attached to MR fluid clutch apparatus 10A using a pulley system. Cable 200A is then routed using redirection pulleys and attached to the first member 226 in order for the tension in cable 200A to generate a lever arm on the first member 226. A similar system is connected on the other side of the joint using MR fluid clutch apparatus 10B, cable 200B and another redirection pulley 223. By generating tension on the cables 200A and 200B, the force on the first member 226 may be generated and the first member 226 may move accordingly. Standard bearings and a gimbal-type joint may be used between chassis 227 and the first member 226. This results in an antagonistic system acting on the first member 226. Because the actuators are not localised at the joint, they do not increase the inertia of the parts in movement and because the MR fluid actuator unit may provide high bandwidth force control, the result may be a highly controllable robotic arm 220 with reduced inertia and with high bandwidth. In the illustrated embodiment, a cable system is shown but other transmission mechanisms may be considered (chain, belt, hydraulics . . . ). In some other instance a biasing member or gravity may be used in lieu of the second MR fluid clutch apparatus and still provide antagonistic force control to the robotic arm 220. Similar cable system routed in additional redirection pulley may provide antagonistic force on the second member 225 and end effector 224. Additionally, a three DOF cable system is illustrated but additional DOF may also be provided. DOF may be rotational and/or translational.

Figure 21:
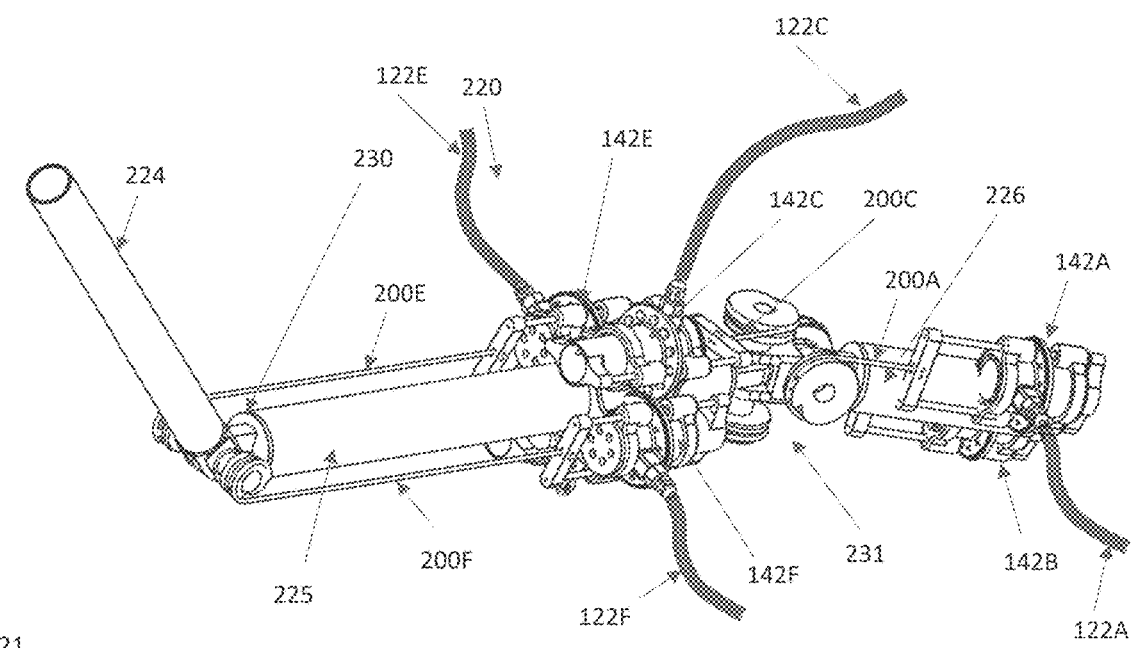
FIG. 21 is a perspective view of a wearable robotic arm with a two degree-of-freedom (DOF) joint actuated with a hybrid hydraulic/cable system powered by MR fluid actuators.

FIG. 21 is a schematic view of a robotic arm 220 that is actuated using a hybrid cable-hydraulic system similar to the one used on the wearable devices of FIG. 12 to FIG. 19, whereby like reference numerals may illustrate like components, with affixed letters A-F relating the components to a given set as in the description of the previous embodiments. Robotic arm 220 may have multiple joints 230 and 231. In the shown embodiment, joint 230 has a single DOF and joint 231 has two DOFs.

Figure 22:
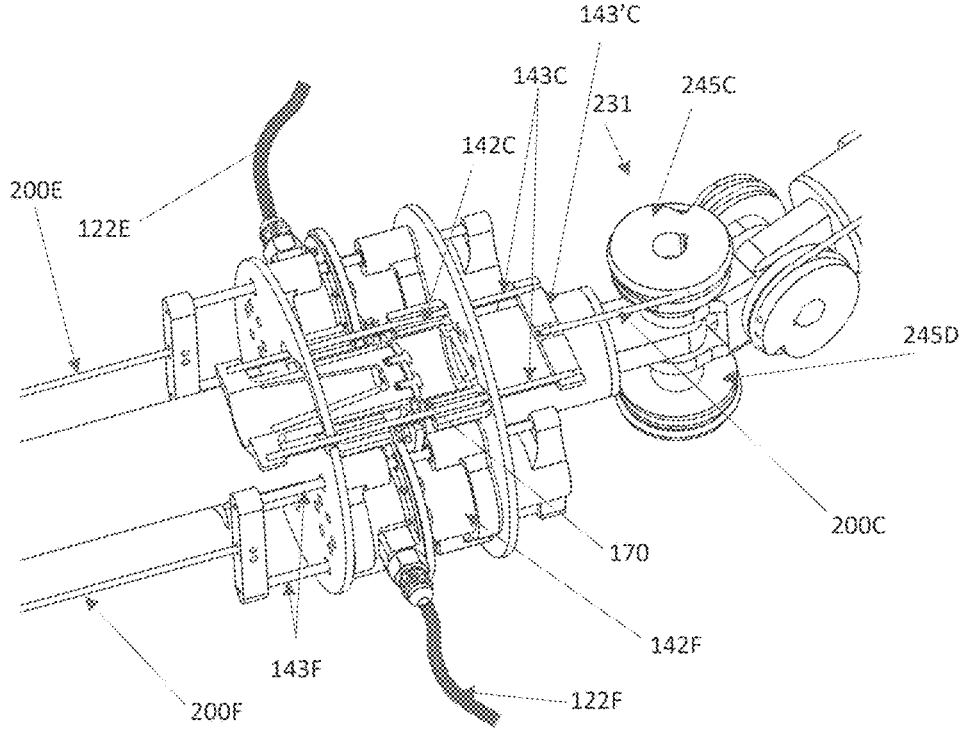
FIG. 22 is an enlarged view of the two DOF joint of the wearable device of FIG. 21 showing the hybrid/cable system.

FIG. 22 depicts an enlargement of the two DOF joint 231. The two DOF joint 231 is shown as gimbal type, but other joint arrangements are contemplated (e.g., universal, spherical). The hydraulic transmission shown is using rolling diaphragms pistons 142 but other types of piston (i.e. dual action push-pull piston, conventional pistons, . . . ) may also be used. In the illustrated embodiment, hydraulic fluid pressure may come from the tubes 122, generating a pressure in the pistons 142. Pressure may generate piston displacement and consequently piston rods 143 displacement. Piston rods 143 may be linked to piston cross member 143' that is connected to cable 200 generating a moment at the joint by acting on a pulley 245 that transfers the moment to the adjacent member. Piston 142 may be located on either side of the joint as long as a moment is generated between the two adjacent members or a member that is remotely located, using similar redirection pulleys as the one shown on the cable system of FIGS. 20A and 20B. Again, two pistons may create antagonistic forces on a joint or other biasing forces may be used. Pistons with push action coupled to linkages and without cables may also be used.

Figure 23:
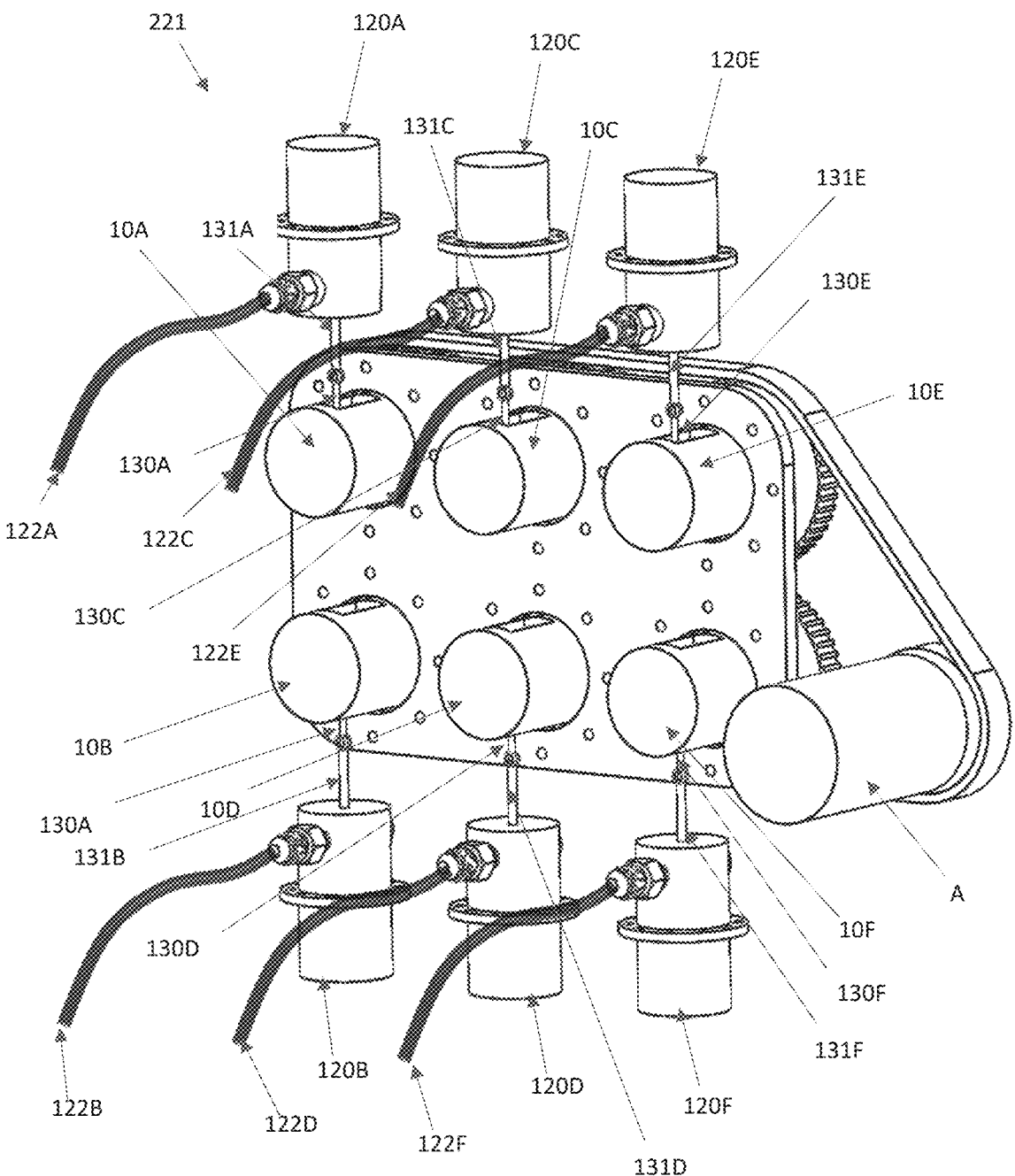
FIG. 23 is a schematic view of a power unit that may be used to actuate the wearable robotic arm of FIG. 21 and using a cable system to actuate hydraulic pistons.

FIG. 23 shows a power unit that may be used to control the robotic arm 220 of FIG. 21. The power unit may be installed directly on the human (in a backpack arrangement as in FIG. 20A) or in a near proximity of the user wearing the robotic arm (e.g., structure, station, ground, vehicle, trolley). Actuation of the cylinders is achieved using a cable system similar to the one used in the power unit of FIG. 13. In FIG. 23, the cable system may have a direct action or a reduction ratio, as in the embodiment of FIG. 13. In the shown embodiment, there are six MR fluid clutch apparatuses 10 that may control up to 6 DOFs. The six MR fluid clutch apparatuses 10 may also be used to control three antagonistic DOFs. In the shown embodiment, the MR fluid clutch apparatuses 10 may be powered by a single power source A, although multiple power sources may also be present. Hydraulic fluid is routed in tubes 122. The pressure and hence the fluid displacement may be controlled individually in each tube 122 by selectively actuating each MR fluid clutch apparatuses 10. One or multiple MR fluid clutch apparatuses 10 may be actuated simultaneously to provide high bandwidth control of all the DOF of the robotic arm 220 of FIG. 21.

Figure 24:
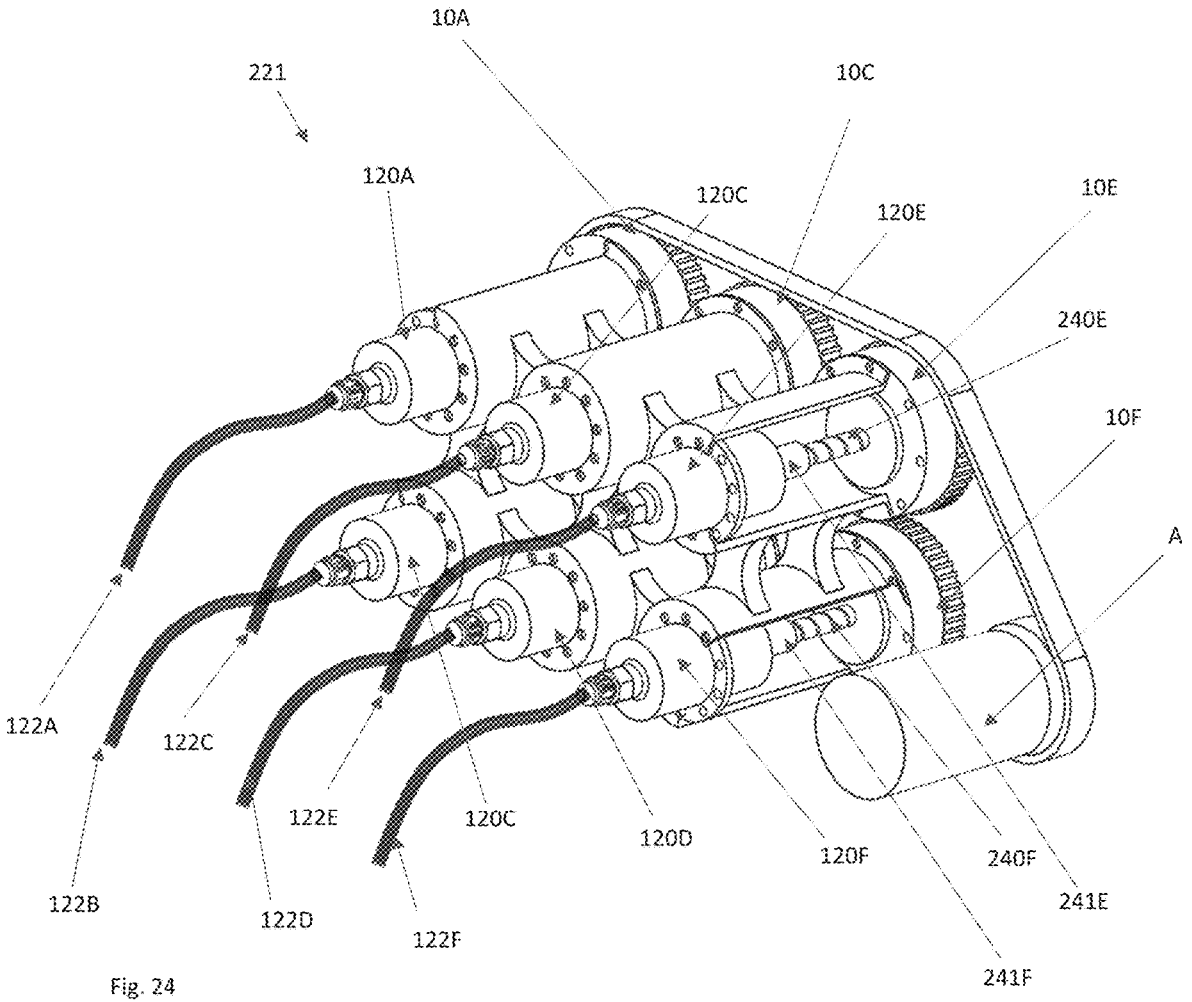
FIG. 24 is a schematic view of a power unit that may be used to actuate the wearable robotic arm of FIG. 21 and using ball screw to actuate hydraulic pistons.

FIG. 24 shows a power unit similar to the one of FIG. 23 but with a ball screw mechanism installed between the piston and the rotary MR fluid clutch apparatus 10. A ball screw mechanism is shown but other type of reduction mechanisms (i.e., rack and pinion, gear system, . . . ) may also be used. The MR fluid clutch apparatuses 10 each drive a screw 240 operatingly supporting a threaded nut 241 of a ball screw reduction mechanism in order to push or pull on the piston rod (not shown) attached to the threaded nut 241. The movement of the piston rod generates pressure in the piston 120 that will be transferred to the piston 142 located on the wearable robotic arm 220 of FIG. 21, via the conduits 122. In the shown embodiment, the MR fluid clutch apparatuses 10 are each connected to a respective screw 240 of a ball screw system but a reverse system where the MR fluid clutch apparatuses 10 act directly on a threaded nut and where the threaded rod is connected to the piston rod is also contemplated.

Figure 25:
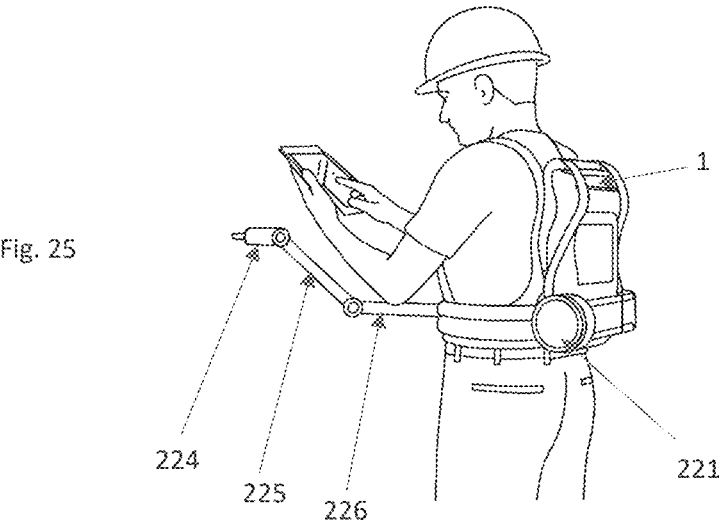
FIG. 25 is showing a user wearing a robotic wearable arm to perform a task while actuated by MR fluid actuators in accordance with the present disclosure.

FIG. 25 shows the robotic arm 220 of FIG. 21 mounted on a human and where the power unit 221 is mounted directly on the human in a backpack arrangement. The power unit 221 may also be located remotely (not on the human) to reduce the weight that the human body has to support. With the high bandwidth of the MR fluid clutch apparatuses 10 combined with the ability of a hydraulic transmission system like the one demonstrated, the wearable robotic arm may be of high bandwidth and work well when installed directly on a human being.

In all wearable robotic arms, one or multiple MR fluid clutches apparatuses 10 may be of the closed or partially closed type of FIGS. 6 and 7 in order to have the joints of the robotic arm 220 blocked or constrained from moving when not powered.

What is claimed is:
1. A system comprising:
two wearable devices, each of the two wearable devices including
    a first body interface adapted to be secured to a first bodily part,
    at least a second body interface adapted to be secured to a second bodily part separated from the first bodily part by a physiological joint;

a magnetorheological (MR) fluid actuator unit comprising
at least one power source,
at least one MR fluid clutch apparatus receiving torque
from the at least one power source, the at least one
MR fluid clutch apparatus operable to generate a
variable amount of torque transmission when sub-
jected to a magnetic field; and
a transmission coupling the MR fluid actuator unit to a
respective one of the wearable device for converting
torque from the MR fluid actuator unit to relative
movement of the body interfaces with respect to one
another;
wherein one of the wearable devices is a right leg exo-
skeleton, and another one of the wearable devices is a
left leg exoskeleton.

2. The system according to claim 1, wherein the first body
interface is a shank body interface adapted to be secured to
a shank of a user.

3. The system according to claim 2, wherein the second
body interface is a foot body interface adapted to be secured
to a foot or footwear of the user.

4. The system according to claim 1, wherein the at least
one power source is an electric motor.

5. The system according to claim 1, wherein each of the
MR fluid actuator units is located remotely from a respective
one of the wearable devices.

6. The system according to claim 5, wherein each of the
MR fluid actuator units is mounted on a dorsal support
adapted to be worn by a user.

7. The system according to claim 1, wherein the trans-
mission includes a cable between the first body interface and
the second body interface, for exerting a pulling action on
the second body interface.

8. A system comprising:
at least one wearable device including
a first body interface adapted to be secured to a first
bodily part,
at least a second body interface adapted to be secured
to a second bodily part separated from the first bodily
part by a physiological joint;
a magnetorheological (MR) fluid actuator unit comprising
at least one power source,
at least one MR fluid clutch apparatus receiving torque
from the at least one power source, the at least one
MR fluid clutch apparatus operable to generate a
variable amount of torque transmission when sub-
jected to a magnetic field; and
a transmission coupling the MR fluid actuator unit to
the wearable device for converting torque from the
MR fluid actuator unit to relative movement of the
body interfaces with respect to one another;
wherein the MR fluid actuator unit is located remotely
from the wearable device as mounted on a dorsal
support adapted to be worn by a user.

9. The system according to claim 8, wherein the first body
interface is a shank body interface adapted to be secured to
a shank of a user.

10. The system according to claim 9, wherein the second
body interface is a foot body interface adapted to be secured
to a foot or footwear of the user.

11. The system according to claim 8, wherein the first
body interface is an upper arm body interface adapted to be
secured to an upper arm of a user.

12. The system according to claim 11, wherein the second
body interface is a lower arm interface adapted to be secured
to a lower arm of the user.

13. The system according to claim 12, further comprising
a third body interface connected to the first body interface by
one said joint, the third body interface being a shoulder body
interface adapted to be secured to a shoulder of the user.

14. The system according to claim 8, wherein the at least
one power source is an electric motor.

15. The system according to claim 8, wherein the trans-
mission includes a cable between the first body interface and
the second body interface, for exerting a pulling action on
the second body interface.

16. A system comprising:
at least one wearable device including
a first body interface adapted to be secured to a first
bodily part,
at least a second body interface adapted to be secured
to a second bodily part separated from the first bodily
part by a physiological joint;
a magnetorheological (MR) fluid actuator unit comprising
at least one power source,
at least one MR fluid clutch apparatus receiving torque
from the at least one power source, the at least one
MR fluid clutch apparatus operable to generate a
variable amount of torque transmission when sub-
jected to a magnetic field; and
a transmission coupling the MR fluid actuator unit to
the wearable device for converting torque from the
MR fluid actuator unit to relative movement of the
body interfaces with respect to one another wherein
the first body interface is a shank body interface
adapted to be secured to a shank of a user.

17. The system according to claim 16, wherein the second
body interface is a foot body interface adapted to be secured
to a foot or footwear of the user.

18. The system according to claim 16, wherein the at least
one power source is an electric motor.

19. The system according to claim 16, wherein the trans-
mission includes a cable between the first body interface and
the second body interface, for exerting a pulling action on
the second body interface.

* * * * *